US008304441B2

(12) United States Patent
Colca et al.

(10) Patent No.: US 8,304,441 B2
(45) Date of Patent: Nov. 6, 2012

(54) THIAZOLIDINEDIONE ANALOGUES FOR THE TREATMENT OF METABOLIC DISEASES

(75) Inventors: Gerard R. Colca, Kalamazoo, MI (US); Robert C. Gadwood, Portage, MI (US); Tim Parker, Portage, MI (US)

(73) Assignee: Metabolic Solutions Development Company, LLC, Kalamazoo, MI (US)

( * ) Notice: Subject to any disclaimer, the term of this patent is extended or adjusted under 35 U.S.C. 154(b) by 0 days.

(21) Appl. No.: 13/279,657

(22) Filed: Nov. 16, 2011

(65) Prior Publication Data
US 2012/0129896 A1 May 24, 2012

Related U.S. Application Data

(62) Division of application No. 12/677,541, filed as application No. PCT/US2008/010723 on Sep. 15, 2008, now Pat. No. 8,067,450.

(60) Provisional application No. 60/972,639, filed on Sep. 14, 2007.

(51) Int. Cl.
*A61K 31/426* (2006.01)
*C07D 277/04* (2006.01)
(52) U.S. Cl. .................................. 514/369; 548/183
(58) Field of Classification Search ............... 514/369; 548/183
See application file for complete search history.

(56) References Cited

U.S. PATENT DOCUMENTS

| 4,582,839 | A | 4/1986 | Meguro et al. |
| 4,687,777 | A | 8/1987 | Meguro et al. |
| 4,725,610 | A | 2/1988 | Meguro et al. |
| 5,304,212 | A | 4/1994 | Czeisler et al. |
| 5,441,971 | A | 8/1995 | Sohda et al. |
| 5,886,026 | A | 3/1999 | Hunter et al. |
| 5,929,101 | A | 7/1999 | Colca |
| 6,099,562 | A | 8/2000 | Ding et al. |
| 6,693,106 | B2 | 2/2004 | Rahbar et al. |
| 2007/0043094 | A1 | 2/2007 | Wizel et al. |
| 2007/0078170 | A1 | 4/2007 | Khanduri et al. |
| 2008/0319024 | A1 | 12/2008 | Greil et al. |
| 2009/0137638 | A1 | 5/2009 | Colca et al. |
| 2009/0143441 | A1 | 6/2009 | Colca |
| 2009/0143442 | A1 | 6/2009 | Colca et al. |

FOREIGN PATENT DOCUMENTS

| EP | 0008203 | 2/1980 |
| EP | 0549365 | 6/1993 |
| EP | 0753298 | 1/1997 |
| WO | WO 86/02073 | 4/1986 |
| WO | WO 92/18501 | 10/1992 |
| WO | WO 01/00579 | 1/2001 |
| WO | WO 01/82916 | 11/2001 |
| WO | WO 02/088120 | 11/2002 |
| WO | WO 2004/007490 | 1/2004 |
| WO | WO 2004/101561 | 11/2004 |
| WO | WO 2006/035954 | 4/2006 |
| WO | WO 2007/109024 | 9/2007 |
| WO | WO 2007/109037 | 9/2007 |
| WO | WO 2007/109088 | 9/2007 |
| WO | WO 2009/038681 | 3/2009 |
| WO | WO 2010/105048 | 9/2010 |

OTHER PUBLICATIONS

LAN, GPR119 is required for physiological regulation of glucagon-like peptide-1 secretion but not for metabolic homeostasis, 2009, Journal of Endocrinology, vol. 201, p. 219-230.*
Pioglitazone—http://www.medicinenet.com/script/main/art.asp?articlekey=11577, retrieved Mar. 13, 2012.*
Agarwal, Rajiv, "Anti-Inflammatory Effects of Short-Term Pioglitazone Therapy in Men with Advanced Diabetic Nephropathy", American Journal of Physiology—Renal Physiology, vol. 290, No. 3 (2006). pp. F600-F605.
Berge, S.M., "Pharmaceutical Salts", Journal Pharmaceutical Sciences, vol. 66, No. 1 (1977), pp. 1-19.
Blocker, <http://dictionary.reference.com/browse/blocker>, accessed Apr. 6, 2011, Office Action Summary dated Apr. 13, 2011 for U.S. Appl. No. 12/677,541.
Campbell, I. W., "Pioglitazone—An Oral Antidiabetic Agent and Metabolic Syndrome Modulator, Can Theory Translate into Practice?", British Journal of Diabetes and Vascular Disease, Medinews, GB vol. 5, No. 4 (2005), pp. 209-216.
Carpenter, Donald, E., et al., "Process Development and Scale-Up of the Potential Thiazolidinedione Antidiabetic Candidate PNU-91325", Organic Process Research and Development, American Chemical Society, (2002), vol. 6, pp. 721-728.
Colca, J. R., et al., "What has Prevented the Expansion of Insulin Sensitisers?", Expert Opinion on Investigational Drugs, 2006, United Kingdom, vol. 15, No. 3 (2006), pp. 205-210.
Colca, Jerry R., "Insulin sensitizers may prevent metabolic inflammation", Biochemical Pharmacology, Pergamon, Oxford, GB, vol. 72, No. 2, Jul. 14, 2006, pp. 125-131, XP025043395, ISSN: 0006-2952.
Colca, Jerry R., et al., "Identification of a Novel Mitochondrial Protein ("mitoNEET") cross-linked specifically by a thiazolidinedione photoprobe", American Journal of Physiology, Endocrinology and Metabolism, Feb. 2004, vol. 286, No. 2, pp. E252-E260, XP002997343, ISSN: 0193-1849.
Diuretic, <http://www.medterms.com/script/main/art.asp?articlekey=7103>, accessed Apr. 6, 2011, Office Action Summary dated Apr. 13, 2011 for U.S. Appl. No. 12/677,541.
Feinstein, D.L., "Receptor-independent actions of PPAR thiazolidinedione agonists: Is mitochondrial function the key?" Biochemical Pharmacology, Pergamon, Oxford, GB, vol. 70, No. 2, Jul. 15, 2005, pp. 177-188.
Freireich, D.L., "Quantative Comparisons of Toxicity of Anticancer Agents in Mouse, Rate, Hamster, Dog, Monkey and Man", Cancer Chemotherapy Reports, vol. 50, No. 4 (1966), p. 219-244.

(Continued)

*Primary Examiner* — Golam M M Shameem
*Assistant Examiner* — Karen Cheng
(74) *Attorney, Agent, or Firm* — Honigman Miller Schwartz and Cohn LLP; Andrew N. Weber; Jonathan P. O'Brien

(57) ABSTRACT

The present invention relates to thiazolidinedione analogues that are useful for treating hypertension, diabetes, and inflammatory diseases.

9 Claims, No Drawings

OTHER PUBLICATIONS

Geldmacher, D.S., "Pioglitazone in Alzheimer's Disease: Rationale and Clinical Trial Design", Neurobiology of Aging, Tarrytown, NY, US, vol. 25 (2004), pp. S211-S212.

Gerber, P., "Effects of Pioglitazone on Metabolic Control and Blood Pressure: A Randomized Study in Patients with Type 2 Diabetes Mellitus", Current Medical Research and Opinion, Hants, GB, vol. 19, No. 6 (2003), pp. 532-539.

Harrigan, George G., et al., "PNU-91325 Increases Fatty Acid Syntheses from Glucose and Mitochondrial Long Chain Fatty Acid Degradation: A Comparative Tracer-Based Metabolomics Study with Rosiglitazone and Piolitazone in hepG2 Cells", Metabolomics, Kluwer Academic Publishers-Plenum Publishers, NE, vol. 2, No. 1 (2006) pp. 21-29.

Hofmann, C., "Glucose Transport Deficiency Corrected by Treatment with the Oral Anti-Hyperglycemic Agent Pioglitazone", Endocrinology, 129 (1991), pp. 1915-1925.

Inhibitor, <http://www.biology-online.org/dictionary/Inhibitor>, accessed Apr. 6, 2011, Office Action Summary dated Apr. 13, 2011 for U.S. Appl. No. 12/677,541.

International Search Report for PCT/US2007/006321 dated Sep. 3, 2007.

International Search Report for PCT/US2007/006385 dated Sep. 10, 2007.

International Search Report for PCT/US2007/006508 dated Sep. 7, 2007.

International Search Report for PCT/US2008/010723 dated Mar. 2, 2009.

International Search Report for PCT/US2010/026971 dated Jul. 22, 2010.

International Search Report for PCT/US2010/060439 dated May 23, 2011.

International Search Report for PCT/US2010/060449 dated Mar. 7, 2011.

International Search Report for PCT/US2010/060453 dated Mar. 28, 2011.

International Search Report for PCT/US2010/060459 dated Mar. 2, 2011.

International Search Report for PCT/US2011/024732 dated May 20, 2011.

Kulkarni, Santosh S., et al., "Three-Dimensional Quantitative Structure Activity Relationship (3-D-QSAR) of Antihyperglycemic Agents" Bioorganic & Medicinal Chemistry, Elsevier Science Ltd, GB, vol. 7 (1999), pp. 1475-1485.

Lehmann, J.M., "An Antidiabetic Thiazolidinedione is a High Affinity Ligand for Peroxisome Proliferator-activated Receptor y (PPARy)", The Journal of Biological Chemistry, vol. 270, No. 22, 1995, pp. 12953-12956.

Matsusue, K., "Liver Specific Disruption of PPAR in Leptin-Deficient Mice Improves Fatty Liver but Aggravates Diabetic Phenotypes", J. Clim. Invest., 111 (2003), p. 737.

Oguchi, M., et al., "Molecular Design, Synthesis, and hypoglycemic Activity of a Series of Thiazolidine-2, 4-diones", Journal of Medicinal Chemistry, (2000)vol. 43 No. 16, pp. 3052-3066.

Pershadsingh, H., "Effect of Pioglitazone Treatment in a patient with Secondary Multiple Sclerosis", Journal of Neuorinflammation Biomed Central Ltd, London, GB, vol. 1, No. 1 (2004), p. 3.

Pershadsingh, H., "Peroxisome Proliferator-Activated Receptor-Gamma: Therapeutic Target for Diseases Beyond Diabetes: Quo Vadis?" Expert Opinion on Investigational Drugs, vol. 13, No. 3 (2004), pp. 215-228.

Sohda, T., "Studies on Antidiabetic Agents. Synthesis and Hypoglycemic Activity of 5-[4-(Pyridylalkoxy)Benzyl]-2,4-Thiazolidinediones", Arzneimittel Forshung Drug Research, ECV Editio. Cantor Verlag, Aulendoef, DE, vol. 40, No. 1 (1990), pp. 37-42.

Sohda, T., et al., "Studies on Antidiabetic Agents. II. Synthesis of 5-[4-(1-Methylcyclohexylmethoxy)-benzyl] thiazolidine-2,4-dione (ADD-3878) and Its Derivatives", Chemical and Pharmaceutical Bulletin, Pharmaceutical Society of Japan, Tokyo, (1982) vol. 30, No. 10, pp. 3580-3600.

Statin, <http://www.amswers.com/topic/statin>, accessed Apr. 6, 2011, Office Action Summary dated Apr. 13, 2011 for U.S. Appl. No. 12/677,541.

Tanis, S. P., et al., "Synthesis and Biological Activity of Metabolites of the Antidiabetic, Antihyperglycemic Agent Pioglitazone", Journal of Medicinal Chemistry, American Chemical Society, US, vol. 39, No. 26, 1996, pp. 5053-5063.

Vosper, H., "The Peroxisome Proliferators Activated Receptor D is Required for the Differentiation of THP-1 Moncytic Cells by Phorbol Ester", Nuclear Receptor, I (2003), p. 9.

Willi, S.M., "Effective Use of Thiazolidinedione for the Treatment of Glucocorticoid-Induced Diabetes", Diabetes Research and Clinical Practice, vol. 58, No. 2 (2002), pp. 87-96 & pp. 91-94.

Yamamoto, Shigeki, et al., "Effects of Pioglitazone on Steroid-Induced Diabetes Mellitus", Journal of the Japan Diabetes Society, vol. 47, No. 8, Aug. 2004, pp. 643-648.

* cited by examiner

THIAZOLIDINEDIONE ANALOGUES FOR THE TREATMENT OF METABOLIC DISEASES

CLAIM OF PRIORITY

This U.S. Patent Application is a divisional of U.S. Ser. No. 12/677,541, which was filed May 19, 2010, now U.S. Pat. No. 8,067,450 and claims the priority of PCT Application No. PCT/US2008/010723, filed Sep. 15, 2008, and U.S. Application No. 60/972,639, filed Sep. 14, 2007. All of these documents are incorporated herein by reference in their entirety.

TECHNICAL FIELD OF THE INVENTION

The present invention provides a pharmaceutical composition that includes selective thiazolidinedione analogs for use in treating and preventing diabetes, hypertension, diabetes, and inflammatory diseases and inflammatory diseases.

BACKGROUND OF THE INVENTION

Over the past several decades, scientists have postulated that PPARγ is the generally accepted site of action for insulin sensitizing thiazolidinedione compounds.

Peroxisome Proliferator Activated Receptors (PPARs) are members of the nuclear hormone receptor super family, which are ligand-activated transcription factors regulating gene expression. PPARs have been implicated in autoimmune diseases and other diseases, i.e diabetes mellitus, cardiovascular and gastrointestinal disease, and Alzheimer's disease.

PPARγ is a key regulator of adipocyte differentiation and lipid metabolism. PPARγ is also found in other cell types including fibroblasts, myocytes, breast cells, human bone-marrow precursors, and macrophages/monocytes. In addition, PPARγ has been shown in macrophage foam cells in atherosclerotic plaques.

Thiazolidinediones, developed originally for the treatment of type-2 diabetes, generally exhibit high-affinity as PPARγ ligands. The finding that thiazolidinedones might mediate their therapeutic effects through direct interactions with PPARγ helped to establish the concept that PPARγ is a key regulator of glucose and lipid homeostasis. However, compounds that involve the activation of PPARγ also trigger sodium reabsorption and other unpleasant side effects.

SUMMARY OF THE INVENTION

In general, the invention relates to compounds that have reduced binding and activation of the nuclear transcription factor PPARγ. Compounds exhibiting PPARγ activity induce transcription of genes that favor sodium re-adsorption. The compounds of this invention have reduced binding or activation of the nuclear transcription factor PPARγ, do not augment sodium re-absorption, and are therefore more useful in treating hypertension, diabetes, and inflammatory diseases. Advantageously, the compounds having lower PPARγ activity exhibit fewer side effects than compounds having higher levels of PPARγ activity. Most specifically, by lacking PPARγ binding and activation activity these compounds are particularly useful for treating hypertension, diabetes, and inflammatory diseases both as single agents and in combination with other classes of antihypertensive agents. As hypertension, diabetes, and inflammatory diseases is a major risk factor in diabetes and prediabetes, these compounds are also useful for the treatment and prevention of diabetes and other inflammatory diseases.

In one aspect, the present invention provides a pharmaceutical composition useful in treating hypertension, diabetes, and inflammatory diseases comprising a compound of formula I:

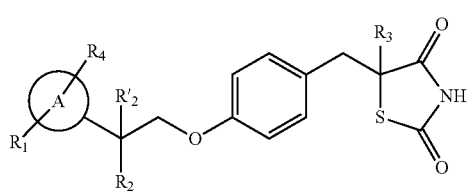

or a pharmaceutically acceptable salt thereof, wherein:

Each of $R_1$ and $R_4$ is independently selected from H, halo, aliphatic, and alkoxy, wherein the aliphatic and alkoxy are optionally substituted with 1-3 of halo;

$R_2$ is halo, hydroxy, or optionally substituted aliphatic, and $R'_2$ is H, or $R_2$ and $R'_2$ together form oxo;

$R_3$ is H; and

Ring A is phenyl.

Another aspect of the present invention provides methods of treating hypertension, diabetes, and inflammatory diseases with a pharmaceutical composition comprising a compound of formula I and a pharmaceutically acceptable carrier.

Another aspect of this invention provides pharmaceutical compositions comprising a compound of formula I and at least one diuretic, such as hydrocholothiazide. Other aspects provide pharmaceutical compositions useful for treating hypertension, diabetes, and inflammatory diseases comprising a compound of formula I and one or more agents that limit the activity of the renin-angiotensin system such as angiotensin concerting enzyme inhibitors, i.e. ACE inhibitors, e.g. ramipril, captopril, enalapril, or the like, and/or angiotensin II receptor blockers, i.e. ARBs, e.g. candesartan, losartan, olmesartan, or the like; and/or renin inhibitors. Still other aspects provide a useful pharmaceutical composition for treating hypertension, diabetes, and inflammatory diseases comprising a compound of formula I and compounds that limit hypertension, by alternate means including β-adrenergic receptor blockers and calcium channel blockers, e.g., amlodipine.

This invention also provides pharmaceutical combinations containing a compound of formula I and a lipid lowering agent. Compounds of formula I, because of their PPARγ-sparing properties and beneficial effects on lipids to lower triglycerides and elevate HDL cholesterol, are particularly useful in combination with one or more statin, i.e., HMG-CoA reductase inhibitor, e.g., atorvastatin, cerivastatin, fluvastatin, lovastatin, mevastatin, simvastatin, rosuvastatin, pravastatin, or any pharmaceutically acceptable combination thereof.

In another aspect, the invention relates to insulin sensitizers that have reduced binding and activation of the nuclear transcription factor PPARγ and therefore produce reduced sodium re-absorption and fewer dose-limiting side effects. Thus, the compounds of formula I are substantially more effective to treat and prevent diabetes and other metabolic inflammation mediated diseases including all aspects of insulin resistance associated with metabolic syndrome including dyslipidemia and central obesity. The compounds of formula I are also useful for treating other inflammatory diseases such as rheumatoid arthritis, lupus, myasthenia gravis, vasculitis, Chronic Obstructive Pulmonary Disease (COPD), and inflammatory bowel disease as well as neurodegenerative diseases such as Alzheimer's disease, Parkinson's disease, multiple schlerosis, acute allergic reactions, transplant rejections, central obesity, dyslipidemia, prediabetes and diabetes.

In another aspect, the present invention provides pharmaceutical compositions comprising a compound of formula I and metformin.

In still another aspect, the invention provides pharmaceutical compositions comprising a compound of formula I, a second agent, a pharmaceutically acceptable carrier, wherein the second agent is selected from dipeptidyl peptidase IV, i.e., DPP-4, inhibitors, e.g., sitagliptin, vildagliptin, or the like; statins, i.e., HMG-CoA reductase inhibitor, e.g., atorvastatin, cerivastatin, fluvastatin, lovastatin, mevastatin, simvastatin, rosuvastatin, pravastatin, or any pharmaceutically acceptable combination thereof; GLP-1 and -2 agonists; or combinations thereof.

In still another aspect, the invention provides a combination of compound of formula I and a glucocorticoid agonist which is useful for treating a number of inflammatory diseases and conditions including therapies of suppressing the immune response, preventing transplant rejections, and treating autoimmune diseases. Exemplary diseases and conditions, include rheumatoid arthritis, lupus, myasthenia gravis, muscular dystrophy vasculitis, multiple schlerosis, Chronic Obstructive Pulmonary Disease (COPD), inflammatory bowel disease, treatment of acute allergic reactions, and transplant rejection.

DETAILED DESCRIPTION OF THE INVENTION

As used herein, the following definitions shall apply unless otherwise indicated.

I. Definitions

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention.

As used herein, the term "glucocorticoid agonist" refers to steroid hormones characterized by their ability to bind with the cortisol receptor. Examples of glucocorticoid agonists include, but are not limited to, Hydrocortisone, Cortisone acetate, Prednisone, Prednisolone, Methylprednisolone, Dexamethasone, Betamethasone, Triamcinolone, Beclometasone, Fludrocortisone acetate, Deoxycorticosterone acetate (DOCA), and Aldosterone.

As used herein the term "aliphatic" encompasses the terms alkyl, alkenyl, alkynyl, each of which being optionally substituted as set forth below.

As used herein, an "alkyl" group refers to a saturated aliphatic hydrocarbon group containing 1-12 (e.g., 1-8, 1-6, or 1-4) carbon atoms. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, or 2-ethylhexyl. An alkyl group can be substituted (i.e., optionally substituted) with one or more substituents such as halo, phospho, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, or heterocycloaliphaticamino], sulfonyl [e.g., aliphatic-$SO_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroarylalkoxy, alkoxycarbonyl, alkylcarbonyloxy, or hydroxy. Without limitation, some examples of substituted alkyls include carboxyalkyl (such as HOOC-alkyl, alkoxycarbonylalkyl, and alkylcarbonyloxyalkyl), cyanoalkyl, hydroxyalkyl, alkoxyalkyl, acylalkyl, aralkyl, (alkoxyaryl)alkyl, (sulfonylamino)alkyl (such as (alkyl-$SO_2$-amino)alkyl), aminoalkyl, amidoalkyl, (cycloaliphatic)alkyl, or haloalkyl.

As used herein, an "alkenyl" group refers to an aliphatic carbon group that contains 2-8 (e.g., 2-12, 2-6, or 2-4) carbon atoms and at least one double bond. Like an alkyl group, an alkenyl group can be straight or branched. Examples of an alkenyl group include, but are not limited to allyl, isoprenyl, 2-butenyl, and 2-hexenyl. An alkenyl group can be optionally substituted with one or more substituents such as halo, phospho, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, heterocycloaliphaticamino, or aliphaticsulfonylamino], sulfonyl [e.g., cycloaliphatic-$SO_2$—, or aryl-$SO_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroaralkoxy, alkoxycarbonyl, alkylcarbonyloxy, or hydroxy. Without limitation, some examples of substituted alkenyls include cyanoalkenyl, alkoxyalkenyl, acylalkenyl, hydroxyalkenyl, aralkenyl, (alkoxyaryl)alkenyl, (sulfonylamino)alkenyl (such as (alkyl-$SO_2$-amino)alkenyl), aminoalkenyl, amidoalkenyl, (cycloaliphatic)alkenyl, or haloalkenyl.

As used herein, an "alkynyl" group refers to an aliphatic carbon group that contains 2-8 (e.g., 2-12, 2-6, or 2-4) carbon atoms and has at least one triple bond. An alkynyl group can be straight or branched. Examples of an alkynyl group include, but are not limited to, propargyl and butynyl. An alkynyl group can be optionally substituted with one or more substituents such as aroyl, heteroaroyl, alkoxy, cycloalkyloxy, heterocycloalkyloxy, aryloxy, heteroaryloxy, aralkyloxy, nitro, carboxy, cyano, halo, hydroxy, sulfo, mercapto, sulfanyl [e.g., aliphaticsulfanyl or cycloaliphaticsulfanyl], sulfinyl [e.g., aliphaticsulfinyl or cycloaliphaticsulfinyl], sulfonyl [e.g., aliphatic-$SO_2$—, aliphaticamino-$SO_2$—, or cycloaliphatic-$SO_2$—], amido [e.g., aminocarbonyl, alkylaminocarbonyl, alkylcarbonylamino, cycloalkylaminocarbonyl, heterocycloalkylaminocarbonyl, cycloalkylcarbonylamino, arylaminocarbonyl, arylcarbonylamino, aralkylcarbonylamino, (heterocycloalkyl)carbonylamino, (cycloalkylalkyl)carbonylamino, heteroaralkylcarbonylamino, heteroarylcarbonylamino or heteroarylaminocarbonyl], urea, thiourea, sulfamoyl, sulfamide, alkoxycarbonyl, alkylcarbonyloxy, cycloaliphatic, heterocycloaliphatic, aryl, heteroaryl, acyl [e.g., (cycloaliphatic)carbonyl or (heterocycloaliphatic)carbonyl], amino [e.g., aliphaticamino], sulfoxy, oxo, carboxy, carbamoyl, (cycloaliphatic)oxy, (heterocycloaliphatic)oxy, or (heteroaryl)alkoxy.

As used herein, an "amido" encompasses both "aminocarbonyl" and "carbonylamino". These terms when used alone or in connection with another group refer to an amido group such as —N($R^X$)—C(O)—$R^Y$ or —C(O)—N($R^X$)$_2$, when used terminally, and —C(O)—N($R_X$)— or —N($R_X$)—C(O)—when used internally, wherein $R^X$ and $R^Y$ are defined below. Examples of amido groups include alkylamido (such as alkylcarbonylamino or alkylaminocarbonyl), (heterocycloaliphatic)amido, (heteroaralkyl)amido, (heteroaryl)amido, (heterocycloalkyl)alkylamido, arylamido, aralkylamido, (cycloalkyl)alkylamido, or cycloalkylamido.

As used herein, an "amino" group refers to —$NR^XR^Y$ wherein each of $R^X$ and $R^Y$ is independently hydrogen, aliphatic, cycloaliphatic, (cycloaliphatic)aliphatic, aryl, araliphatic, heterocycloaliphatic, (heterocycloaliphatic)aliphatic, heteroaryl, carboxy, sulfanyl, sulfinyl, sulfonyl, (aliphatic)carbonyl, (cycloaliphatic)carbonyl, ((cycloaliphatic)aliphatic)carbonyl, arylcarbonyl, (araliphatic)carbonyl, (heterocycloaliphatic)carbonyl, ((heterocycloaliphatic)aliphatic)carbonyl, (heteroaryl)carbonyl, or (heteroaraliphatic)carbonyl, each of which being defined herein and being optionally substituted. Examples of amino groups include alkylamino, dialkylamino, or arylamino. When the term "amino" is not the terminal group (e.g., alkylcarbonylamino), it is represented by —$NR^X$—. $R^X$ has the same meaning as defined above.

As used herein, an "aryl" group used alone or as part of a larger moiety as in "aralkyl", "aralkoxy", or "aryloxyalkyl" refers to monocyclic (e.g., phenyl); bicyclic (e.g., indenyl, naphthalenyl, tetrahydronaphthyl, tetrahydroindenyl); and tricyclic (e.g., fluorenyl tetrahydrofluorenyl, or tetrahydroanthracenyl, anthracenyl) ring systems in which the monocyclic ring system is aromatic or at least one of the rings in a bicyclic or tricyclic ring system is aromatic. The bicyclic and tricyclic groups include benzofused 2-3 membered carbocyclic rings. For example, a benzofused group includes phenyl fused with two or more $C_{4-8}$ carbocyclic moieties. An aryl is optionally substituted with one or more substituents including aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; oxo (on a non-aromatic carbocyclic ring of a benzofused bicyclic or tricyclic aryl); nitro; carboxy; amido; acyl [e.g., (aliphatic)carbonyl; (cycloaliphatic)carbonyl; ((cycloaliphatic)aliphatic)carbonyl; (araliphatic)carbonyl; (heterocycloaliphatic)carbonyl; ((heterocycloaliphatic)aliphatic)carbonyl; or (heteroaraliphatic)carbonyl]; sulfonyl [e.g., aliphatic-$SO_2$— or amino-$SO_2$—]; sulfinyl [e.g., aliphatic-S(O)— or cycloaliphatic-S(O)—]; sulfanyl [e.g., aliphatic-S—]; cyano; halo; hydroxy; mercapto; sulfoxy; urea; thiourea; sulfamoyl; sulfamide; or carbamoyl. Alternatively, an aryl can be unsubstituted.

Non-limiting examples of substituted aryls include haloaryl [e.g., mono-, di (such as p,m-dihaloaryl), and (trihalo)aryl]; (carboxy)aryl [e.g., (alkoxycarbonyl)aryl, ((aralkyl)carbonyloxy)aryl, and (alkoxycarbonyl)aryl]; (amido)aryl [e.g., (aminocarbonyl)aryl, (((alkylamino)alkyl)aminocarbonyl)aryl, (alkylcarbonyl)aminoaryl, (arylaminocarbonyl)aryl, and (((heteroaryl)amino)carbonyl)aryl]; aminoaryl [e.g., ((alkylsulfonyl)amino)aryl or ((dialkyl)amino)aryl]; (cyanoalkyl)aryl; (alkoxy)aryl; (sulfamoyl)aryl [e.g., (aminosulfonyl)aryl]; (alkylsulfonyl)aryl; (cyano)aryl; (hydroxyalkyl)aryl; ((alkoxy)alkyl)aryl; (hydroxy)aryl, ((carboxy)alkyl)aryl; (((dialkyl)amino)alkyl)aryl; (nitroalkyl)aryl; (((alkylsulfonyl)amino)alkyl)aryl; ((heterocycloaliphatic)carbonyl)aryl; ((alkylsulfonyl)alkyl)aryl; (cyanoalkyl)aryl; (hydroxyalkyl)aryl; (alkylcarbonyl)aryl; alkylaryl; (trihaloalkyl)aryl; p-amino-m-alkoxycarbonylaryl; p-amino-m-cyanoaryl; p-halo-m-aminoaryl; or (m-(heterocycloaliphatic)-o-(alkyl))aryl.

As used herein, an "araliphatic" such as an "aralkyl" group refers to an aliphatic group (e.g., a $C_{1-4}$ alkyl group) that is substituted with an aryl group. "Aliphatic," "alkyl," and "aryl" are defined herein. An example of an araliphatic such as an aralkyl group is benzyl.

As used herein, an "aralkyl" group refers to an alkyl group (e.g., a $C_{1-4}$ alkyl group) that is substituted with an aryl group. Both "alkyl" and "aryl" have been defined above. An example of an aralkyl group is benzyl. An aralkyl is optionally substituted with one or more substituents such as aliphatic [e.g., alkyl, alkenyl, or alkynyl, including carboxyalkyl, hydroxyalkyl, or haloalkyl such as trifluoromethyl], cycloaliphatic [e.g., cycloalkyl or cycloalkenyl], (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, amido [e.g., aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, or heteroaralkylcarbonylamino], cyano, halo, hydroxy, acyl, mercapto, alkylsulfanyl, sulfoxy, urea, thiourea, sulfamoyl, sulfamide, oxo, or carbamoyl.

As used herein, a "bicyclic ring system" includes 8-12 (e.g., 9, 10, or 11) membered structures that form two rings, wherein the two rings have at least one atom in common (e.g., 2 atoms in common). Bicyclic ring systems include bicycloaliphatics (e.g., bicycloalkyl or bicycloalkenyl), bicycloheteroaliphatics, bicyclic aryls, and bicyclic heteroaryls.

As used herein, a "cycloaliphatic" group encompasses a "cycloalkyl" group and a "cycloalkenyl" group, each of which being optionally substituted as set forth below.

As used herein, a "cycloalkyl" group refers to a saturated carbocyclic mono- or bicyclic (fused or bridged) ring of 3-10 (e.g., 5-10) carbon atoms. Examples of cycloalkyl groups include cyclopropyl, cyclobutyl, cyclopentyl, cyclohexyl, cycloheptyl, adamantyl, norbornyl, cubyl, octahydro-indenyl, decahydro-naphthyl, bicyclo[3.2.1]octyl, bicyclo[2.2.2]octyl, bicyclo[3.3.1]nonyl, bicyclo[3.3.2]decyl, bicyclo[2.2.2]octyl, adamantyl, or ((aminocarbonyl)cycloalkyl)cycloalkyl.

A "cycloalkenyl" group, as used herein, refers to a non-aromatic carbocyclic ring of 3-10 (e.g., 4-8) carbon atoms having one or more double bonds. Examples of cycloalkenyl groups include cyclopentenyl, 1,4-cyclohexa-di-enyl, cycloheptenyl, cyclooctenyl, hexahydro-indenyl, octahydro-naphthyl, cyclohexenyl, cyclopentenyl, bicyclo[2.2.2]octenyl, or bicyclo[3.3.1]nonenyl.

A cycloalkyl or cycloalkenyl group can be optionally substituted with one or more substituents such as phosphor, aliphatic [e.g., alkyl, alkenyl, or alkynyl], cycloaliphatic, (cycloaliphatic) aliphatic, heterocycloaliphatic, (heterocycloaliphatic) aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic)aliphatic) carbonylamino, (aryl)carbonylamino, (araliphatic)carbonylamino, (heterocycloaliphatic)carbonylamino, ((heterocycloaliphatic)aliphatic)carbonylamino, (heteroaryl) carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic)carbonyl, or (heteroaraliphatic)carbonyl], cyano, halo, hydroxy, mercapto, sulfonyl [e.g., alkyl-SO$_2$— and aryl-SO$_2$—], sulfinyl [e.g., alkyl-S(O)—], sulfanyl [e.g., alkyl-S—], sulfoxy, urea, thiourea, sulfamoyl, sulfamide, oxo, or carbamoyl.

As used herein, the term "heterocycloaliphatic" encompasses a heterocycloalkyl group and a heterocycloalkenyl group, each of which being optionally substituted as set forth below.

As used herein, a "heterocycloalkyl" group refers to a 3-10 membered mono- or bicyclic (fused or bridged) (e.g., 5- to 10-membered mono- or bicyclic) saturated ring structure, in which one or more of the ring atoms is a heteroatom (e.g., N, O, S, or combinations thereof). Examples of a heterocycloalkyl group include piperidyl, piperazyl, tetrahydropyranyl, tetrahydrofuryl, 1,4-dioxolanyl, 1,4-dithianyl, 1,3-dioxolanyl, oxazolidyl, isoxazolidyl, morpholinyl, thiomorpholyl, octahydrobenzofuryl, octahydrochromenyl, octahydrothiochromenyl, octahydroindolyl, octahydropyrindinyl, decahydroquinolinyl, octahydrobenzo[b]thiopheneyl, 2-oxa-bicyclo[2.2.2]octyl, 1-aza-bicyclo[2.2.2] octyl, 3-aza-bicyclo[3.2.1]octyl, and 2,6-dioxa-tricyclo [3.3.1.0$^{3,7}$]nonyl. A monocyclic heterocycloalkyl group can be fused with a phenyl moiety to form structures, such as tetrahydroisoquinoline, which would be categorized as heteroaryls.

A "heterocycloalkenyl" group, as used herein, refers to a mono- or bicyclic (e.g., 5- to 10-membered mono- or bicyclic) non-aromatic ring structure having one or more double bonds, and wherein one or more of the ring atoms is a heteroatom (e.g., N, O, or S). Monocyclic and bicyclic heterocycloaliphatics are numbered according to standard chemical nomenclature.

A heterocycloalkyl or heterocycloalkenyl group can be optionally substituted with one or more substituents such as phosphor, aliphatic [e.g., alkyl, alkenyl, or alkynyl], cycloaliphatic, (cycloaliphatic)aliphatic, heterocycloaliphatic, (heterocycloaliphatic)aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic) aliphatic)carbonylamino, (aryl)carbonylamino, (araliphatic) carbonylamino, (heterocycloaliphatic)carbonylamino, ((heterocycloaliphatic) aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic) carbonyl, or (heteroaraliphatic)carbonyl], nitro, cyano, halo, hydroxy, mercapto, sulfonyl [e.g., alkylsulfonyl or arylsulfonyl], sulfinyl [e.g., alkylsulfinyl], sulfanyl [e.g., alkylsulfanyl], sulfoxy, urea, thiourea, sulfamoyl, sulfamide, oxo, or carbamoyl.

A "heteroaryl" group, as used herein, refers to a monocyclic, bicyclic, or tricyclic ring system having 4 to 15 ring atoms wherein one or more of the ring atoms is a heteroatom (e.g., N, O, S, or combinations thereof) and in which the monocyclic ring system is aromatic or at least one of the rings in the bicyclic or tricyclic ring systems is aromatic. A heteroaryl group includes a benzofused ring system having 2 to 3 rings. For example, a benzofused group includes benzo fused with one or two 4 to 8 membered heterocycloaliphatic moieties (e.g., indolizyl, indolyl, isoindolyl, 3H-indolyl, indolinyl, benzo[b]furyl, benzo[b]thiophenyl, quinolinyl, or isoquinolinyl). Some examples of heteroaryl are azetidinyl, pyridyl, 1H-indazolyl, furyl, pyrrolyl, thienyl, thiazolyl, oxazolyl, imidazolyl, tetrazolyl, benzofuryl, isoquinolinyl, benzthiazolyl, xanthene, thioxanthene, phenothiazine, dihydroindole, benzo[1,3]dioxole, benzo[b]furyl, benzo[b]thiophenyl, indazolyl, benzimidazolyl, benzthiazolyl, puryl, cinnolyl, quinolyl, quinazolyl, cinnolyl, phthalazyl, quinazolyl, quinoxalyl, isoquinolyl, 4H-quinolizyl, benzo-1, 2,5-thiadiazolyl, or 1,8-naphthyridyl.

Without limitation, monocyclic heteroaryls include furyl, thiophenyl, 2H-pyrrolyl, pyrrolyl, oxazolyl, thazolyl, imidazolyl, pyrazolyl, isoxazolyl, isothiazolyl, 1,3,4-thiadiazolyl, 2H-pyranyl, 4-H-pranyl, pyridyl, pyridazyl, pyrimidyl, pyrazolyl, pyrazyl, or 1,3,5-triazyl. Monocyclic heteroaryls are numbered according to standard chemical nomenclature.

Without limitation, bicyclic heteroaryls include indolizyl, indolyl, isoindolyl, 3H-indolyl, indolinyl, benzo[b]furyl, benzo[b]thiophenyl, quinolinyl, isoquinolinyl, indolizyl, isoindolyl, indolyl, benzo[b]furyl, bexo[b]thiophenyl, indazolyl, benzimidazyl, benzthiazolyl, purinyl,
4H-quinolizyl, quinolyl, isoquinolyl, cinnolyl, phthalazyl, quinazolyl, quinoxalyl, 1,8-naphthyridyl, or pteridyl.

Bicyclic heteroaryls are numbered according to standard chemical nomenclature.

A heteroaryl is optionally substituted with one or more substituents such as aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic) oxy; aryloxy; heteroaryloxy; (araliphatic)oxy; (heteroaraliphatic)oxy; aroyl; heteroaroyl; amino; oxo (on a non-aromatic carbocyclic or heterocyclic ring of a bicyclic or tricyclic heteroaryl); carboxy; amido; acyl [e.g., aliphaticcarbonyl; (cycloaliphatic)carbonyl; ((cycloaliphatic)aliphatic) carbonyl; (araliphatic)carbonyl; (heterocycloaliphatic)carbonyl; ((heterocycloaliphatic)aliphatic)carbonyl; or (heteroaraliphatic)carbonyl]; sulfonyl [e.g., aliphaticsulfonyl or aminosulfonyl]; sulfinyl [e.g., aliphaticsulfinyl]; sulfanyl [e.g., aliphaticsulfanyl]; nitro; cyano; halo; hydroxy; mercapto; sulfoxy; urea; thiourea; sulfamoyl; sulfamide; or carbamoyl. Alternatively, a heteroaryl can be unsubstituted.

Non-limiting examples of substituted heteroaryls include (halo)heteroaryl [e.g., mono- and di-(halo)heteroaryl]; (carboxy)heteroaryl [e.g., (alkoxycarbonyl)heteroaryl]; cyanoheteroaryl; aminoheteroaryl [e.g., ((alkylsulfonyl)amino)heteroaryl and ((dialkyl)amino)heteroaryl]; (amido)heteroaryl [e.g., aminocarbonylheteroaryl, ((alkylcarbonyl)amino)heteroaryl, ((((alkyl)amino)alkyl)aminocarbonyl)heteroaryl, (((heteroaryl)amino)carbonyl)heteroaryl, ((heterocycloaliphatic)carbonyl)heteroaryl, and ((alkylcarbonyl) amino)heteroaryl]; (cyanoalkyl)heteroaryl; (alkoxy)heteroaryl; (sulfamoyl)heteroaryl [e.g., (aminosulfonyl) heteroaryl]; (sulfonyl)heteroaryl [e.g., (alkylsulfonyl) heteroaryl]; (hydroxyalkyl)heteroaryl; (alkoxyalkyl) heteroaryl; (hydroxy)heteroaryl; ((carboxy)alkyl)heteroaryl; ((((dialkyl)amino)alkyl]heteroaryl; (heterocycloaliphatic)

heteroaryl; (cycloaliphatic)heteroaryl; (nitroalkyl)heteroaryl; (((alkylsulfonyl)amino)alkyl)heteroaryl; ((alkylsulfonyl)alkyl)heteroaryl; (cyanoalkyl)heteroaryl; (acyl)heteroaryl [e.g., (alkylcarbonyl)heteroaryl]; (alkyl)heteroaryl, and (haloalkyl)heteroaryl [e.g., trihaloalkylheteroaryl].

A "heteroaraliphatic (such as a heteroaralkyl group) as used herein, refers to an aliphatic group (e.g., a $C_{1-4}$ alkyl group) that is substituted with a heteroaryl group. "Aliphatic," "alkyl," and "heteroaryl" have been defined above.

A "heteroaralkyl" group, as used herein, refers to an alkyl group (e.g., a $C_{1-4}$ alkyl group) that is substituted with a heteroaryl group. Both "alkyl" and "heteroaryl" have been defined above. A heteroaralkyl is optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, "cyclic moiety" and "cyclic group" refer to mono-, bi-, and tri-cyclic ring systems including cycloaliphatic, heterocycloaliphatic, aryl, or heteroaryl, each of which has been previously defined.

As used herein, a "bridged bicyclic ring system" refers to a bicyclic heterocyclicalipahtic ring system or bicyclic cycloaliphatic ring system in which the rings are bridged. Examples of bridged bicyclic ring systems include, but are not limited to, adamantanyl, norbornanyl, bicyclo[3.2.1]octyl, bicyclo[2.2.2]octyl, bicyclo[3.3.1]nonyl, bicyclo[3.2.3]nonyl, 2-oxabicyclo[2.2.2]octyl, 1-azabicyclo[2.2.2]octyl, 3-azabicyclo[3.2.1]octyl, and 2,6-dioxa-tricyclo[3.3.1.0$^{3,7}$] nonyl. A bridged bicyclic ring system can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, an "acyl" group refers to a formyl group or $R^X$—C(O)— (such as alkyl-C(O)—, also referred to as "alkylcarbonyl") where $R^X$ and "alkyl" have been defined previously. Acetyl and pivaloyl are examples of acyl groups.

As used herein, an "aroyl" or "heteroaroyl" refers to an aryl-C(O)— or a heteroaryl-C(O)—. The aryl and heteroaryl portion of the aroyl or heteroaroyl is optionally substituted as previously defined.

As used herein, an "alkoxy" group refers to an alkyl-O— group where "alkyl" has been defined previously.

As used herein, a "carbamoyl" group refers to a group having the structure —O—CO—NR$^X$R$^Y$ or —NR$^X$—CO— O—R$^Z$, wherein R$^X$ and R$^Y$ have been defined above and R$^Z$ can be aliphatic, aryl, araliphatic, heterocycloaliphatic, heteroaryl, or heteroaraliphatic.

As used herein, a "carboxy" group refers to —COOH, —COOR$^X$, —OC(O)H, —OC(O)R$^X$, when used as a terminal group; or —OC(O)— or —C(O)O— when used as an internal group.

As used herein, a "haloaliphatic" group refers to an aliphatic group substituted with 1-3 halogen. For instance, the term haloalkyl includes the group —CF$_3$.

As used herein, a "mercapto" group refers to —SH.

As used herein, a "sulfo" group refers to —SO$_3$H or —SO$_3$R$^X$ when used terminally or —S(O)$_3$— when used internally.

As used herein, a "sulfamide" group refers to the structure —NR$^X$—S(O)$_2$—NR$^Y$R$^Z$ when used terminally and —NR$^X$—S(O)$_2$—NR$^Y$— when used internally, wherein R$^X$, R$^Y$, and R$^Z$ have been defined above.

As used herein, a "sulfonamide" group refers to the structure —S(O)$_2$—NR$^X$R$^Y$ or —NR$^X$—S(O)$_2$—R$^Z$ when used terminally; or —S(O)$_2$—NR$^X$— or —NR$^X$—S(O)$_2$— when used internally, wherein R$^X$, R$^Y$, and R$^Z$ are defined above.

As used herein a "sulfanyl" group refers to —S—R$^X$ used terminally and —S— when used internally, wherein R$^X$ has been defined above. Examples of sulfanyls include aliphatic-S—, cycloaliphatic-S—, aryl-S—, or the like.

As used herein a "sulfinyl" group refers to —S(O)—R$^X$ when used terminally and —S(O)—when used internally, wherein R$^X$ has been defined above. Exemplary sulfinyl groups include aliphatic-S(O)—, aryl-S(O)—, (cycloaliphatic(aliphatic))-S(O)—, cycloalkyl-S(O)—, heterocycloaliphatic-S(O)—, heteroaryl-S(O)—, or the like.

As used herein, a "sulfonyl" group refers to —S(O)$_2$—R$^X$ when used terminally and —S(O)$_2$— when used internally, wherein R$^X$ has been defined above. Exemplary sulfonyl groups include aliphatic-S(O)$_2$—, aryl-S(O)$_2$—, (cycloaliphatic(aliphatic))-S(O)$_2$—, cycloaliphatic-S(O)$_2$—, heterocycloaliphatic-S(O)$_2$—, heteroaryl-S(O)$_2$—, (cycloaliphatic(amido(aliphatic)))-S(O)$_2$— or the like.

As used herein, a "sulfoxy" group refers to —O—SO—R$^X$ or —SO—O—R$^X$, when used terminally and —O—S(O)— or —S(O)—O— when used internally, where R$^X$ has been defined above.

As used herein, a "halogen" or "halo" group refers to fluorine, chlorine, bromine or iodine.

As used herein, an "alkoxycarbonyl," which is encompassed by the term carboxy, used alone or in connection with another group refers to a group such as alkyl-O—C(O)—.

As used herein, an "alkoxyalkyl" refers to an alkyl group such as alkyl-O-alkyl-, wherein alkyl has been defined above.

As used herein, a "carbonyl" refer to —C(O)—.

As used herein, an "oxo" refers to =O.

As used herein, the term "phospho" refers to phosphinates and phosphonates. Examples of phosphinates and phosphonates include —P(O)(R$^P$)$_2$, wherein R$^P$ is aliphatic, alkoxy, aryloxy, heteroaryloxy, (cycloaliphatic)oxy, (heterocycloaliphatic)oxy aryl, heteroaryl, cycloaliphatic or amino.

As used herein, an "aminoalkyl" refers to the structure (R$_X$)$_2$N-alkyl-.

As used herein, a "cyanoalkyl" refers to the structure (NC)-alkyl-.

As used herein, a "urea" group refers to the structure —NR$^X$—CO—NR$^Y$R$^Z$ and a "thiourea" group refers to the structure —NR$^X$—CS—NR$^Y$R$^Z$ when used terminally and —NR$^X$—CO—NR$^Y$— or —NR$^X$—CS—NR$^Y$— when used internally, wherein R$^X$, R$^Y$, and R$^Z$ have been defined above.

As used herein, a "guanidine" group refers to the structure —N=C(N($R^XR^Y$))N($R^XR^Y$) or —$NR^X$—C(=$NR^X$)$NR^XR^Y$ wherein $R^X$ and $R^Y$ have been defined above.

As used herein, the term "amidino" group refers to the structure —C=($NR^X$)N($R^XR^Y$) wherein $R^X$ and $R^Y$ have been defined above.

In general, the term "vicinal" refers to the placement of substituents on a group that includes two or more carbon atoms, wherein the substituents are attached to adjacent carbon atoms.

In general, the term "geminal" refers to the placement of substituents on a group that includes two or more carbon atoms, wherein the substituents are attached to the same carbon atom.

The terms "terminally" and "internally" refer to the location of a group within a substituent. A group is terminal when the group is present at the end of the substituent not further bonded to the rest of the chemical structure. Carboxyalkyl, i.e., $R^X$O(O)C-alkyl is an example of a carboxy group used terminally. A group is internal when the group is present in the middle of a substituent of the chemical structure. Alkylcarboxy (e.g., alkyl-C(O)O— or alkyl-OC(O)—) and alkylcarboxyaryl (e.g., alkyl-C(O)O-aryl- or alkyl-O(CO)-aryl-) are examples of carboxy groups used internally.

As used herein, an "aliphatic chain" refers to a branched or straight aliphatic group (e.g., alkyl groups, alkenyl groups, or alkynyl groups). A straight aliphatic chain has the structure —$[CH_2]_v$—, where v is 1-12. A branched aliphatic chain is a straight aliphatic chain that is substituted with one or more aliphatic groups. A branched aliphatic chain has the structure —$[CQQ]_v$— where Q is independently a hydrogen or an aliphatic group; however, Q shall be an aliphatic group in at least one instance. The term aliphatic chain includes alkyl chains, alkenyl chains, and alkynyl chains, where alkyl, alkenyl, and alkynyl are defined above.

The phrase "optionally substituted" is used interchangeably with the phrase "substituted or unsubstituted." As described herein, compounds of the invention can optionally be substituted with one or more substituents, such as are illustrated generally above, or as exemplified by particular classes, subclasses, and species of the invention. As described herein, the variables $R_1$, $R_2$, and $R_3$, and other variables contained in formulae described herein encompass specific groups, such as alkyl and aryl. Unless otherwise noted, each of the specific groups for the variables $R_1$, $R_2$, and $R_3$, and other variables contained therein can be optionally substituted with one or more substituents described herein. Each substituent of a specific group is further optionally substituted with one to three of halo, cyano, oxo, alkoxy, hydroxy, amino, nitro, aryl, cycloaliphatic, heterocycloaliphatic, heteroaryl, haloalkyl, and alkyl. For instance, an alkyl group can be substituted with alkylsulfanyl and the alkylsulfanyl can be optionally substituted with one to three of halo, cyano, oxo, alkoxy, hydroxy, amino, nitro, aryl, haloalkyl, and alkyl. As an additional example, the cycloalkyl portion of a (cycloalkyl)carbonylamino can be optionally substituted with one to three of halo, cyano, alkoxy, hydroxy, nitro, haloalkyl, and alkyl. When two alkoxy groups are bound to the same atom or adjacent atoms, the two alkxoy groups can form a ring together with the atom(s) to which they are bound.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

The phrase "stable or chemically feasible," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

As used herein, an "effective amount" is defined as the amount required to confer a therapeutic effect on the treated patient, and is typically determined based on age, surface area, weight, and condition of the patient. The interrelationship of dosages for animals and humans (based on milligrams per meter squared of body surface) is described by Freireich et al., Cancer Chemother. Rep., 50: 219 (1966). Body surface area may be approximately determined from height and weight of the patient. See, e.g., Scientific Tables, Geigy Pharmaceuticals, Ardsley, N.Y., 537 (1970). As used herein, "patient" refers to a mammal, including a human.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C— or $^{14}$C-enriched carbon are within the scope of this invention. Such compounds are useful, for example, as analytical tools or probes in biological assays, or as therapeutic agents.

II. Pharmaceutical Compositions

It is commonly believed that efficacious insulin sensitizing compounds must have high PPARγ activity, and conversely, that compounds having reduced PPARγ activity would yield reduced insulin sensitizing activity. Contrary to this belief, thiazolidinedione compounds of the present invention are uniquely effective in treating hypertension, diabetes, and inflammatory diseases and possess a reduced interaction with PPARγ.

Without wishing to be bound by theory, it is believed that metabolic inflammation is a central cause of the numerous key diseases including hypertension, diabetes, and inflammatory diseases. It is further believed that thiazolidinediones of the present invention function to prevent hypertension, diabetes, and inflammatory diseases via a mitochondrial mechanism. Furthermore since the dose limiting side effects due to PPARγ interaction are reduced in compounds of the present invention; especially steroselective isomers, the compounds of formula I are highly useful for treating hypertension, diabetes, and inflammatory diseases.

Additionally, since the thiazolidinedione analogues of the present invention function via a mitochondrial mechanism, the compounds of formula I are useful in treating or preventing all of the disease states wherein metabolic inflammation is the basis of the pathology.

Furthermore since the dose limiting side effects due to PPARγ interaction are reduced in compounds of the present invention; especially steroselective isomers, the compounds of formula I when used in combination with a glucocorticoid agonist can be used for treating inflammatory diseases.

Generic Compositions

The present invention provides pharmaceutical compositions that are useful for treating hypertension, diabetes, and inflammatory diseases comprising a compound of formula I:

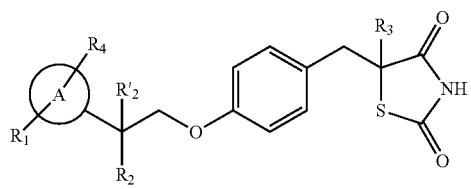

I or a pharmaceutically acceptable salt thereof.

Each of $R_1$ and $R_4$ is independently selected from H, halo, aliphatic, and alkoxy, wherein the aliphatic and alkoxy are optionally substituted with 1-3 of halo.

$R_2$ is halo, hydroxy, or optionally substituted aliphatic, and $R'_2$ is H, or $R_2$ and $R'_2$ together form oxo.

$R_3$ is H.

Ring A is phenyl.

In several embodiments, $R_1$ is H. In some embodiments, $R_1$ is halo, such as F or Cl. In some embodiments, $R_1$ is an aliphatic optionally substituted with 1-3 halo. For instance, $R_1$ specific embodiments, $R_1$ is. $R_1$ is alkoxy. For instance, $R_1$ is methoxy, ethoxy, or —O-isopropyl. In still other embodiments, $R_1$ is alkoxy substitiuted with 1-3 halo. For instance, $R_1$ is —OCHF$_2$ or —OCF$_3$. In each of the foregoing embodiments, $R_1$ can be is substituted at the ortho, meta, or para position on the phenyl ring. In certain embodiments, $R_1$ is substituted at the para or meta position on the phenyl ring.

In several embodiments, $R_4$ is H. In some embodiments, $R_4$ is halo, such as F or Cl. In some embodiments, $R_4$ is an aliphatic optionally substituted with 1-3 halo. For instance, $R_4$ specific embodiments, $R_4$ is. $R_4$ is alkoxy. For instance, $R_4$ is methoxy, ethoxy, or —O-isopropyl. In still other embodiments, $R_4$ is alkoxy substitiuted with 1-3 halo. For instance, $R_4$ is —OCHF$_2$ or —OCF$_3$. In each of the foregoing embodiments, $R_4$ can be is substituted at the ortho, meta, or para position on the phenyl ring. In certain embodiments, $R_4$ is substituted at the para or meta position on the phenyl ring. In some embodiments, $R_1$ and $R_4$ are different substituents. In still other embodiments, $R_1$ and $R_4$ are the same substituent. In some embodiments when $R_1$ is aliphatic, $R_4$ is other than H.

In several embodiments, each of $R_1$ and $R_4$ is independently selected from H, halo, aliphatic, and alkoxy, wherein the aliphatic and alkoxy are optionally substituted with 1-3 of halo, provided that when one of $R_1$ and $R_4$ is H that the other is not ethyl.

In several embodiments, each of $R_1$ and $R_4$ is independently selected from H, halo, aliphatic, and alkoxy, wherein the aliphatic and alkoxy are optionally substituted with 1-3 of halo, provided that when one of $R_1$ and $R_4$ is H that the other is not ethyl substituted at the 4 position of the phenyl.

In several embodiments, $R_2$ is hydrogen, halo, hydroxy, or an optionally substituted $C_{1-6}$ aliphatic. For example, $R_2$ is an optionally substituted straight or branched $C_{1-6}$ alkyl, an optionally substituted straight or branched $C_{2-6}$ alkenyl, or an optionally substituted straight or branched $C_{2-6}$ alkynyl. In other examples, $R_2$ is a $C_{1-6}$ aliphatic optionally substituted with 1-2 hydroxy or halo. In other examples, $R_2$ is a $C_{1-6}$ alkyl optionally substituted with hydroxy. In several other examples, $R_2$ is a methyl, ethyl, propyl, isopropyl, butyl, tert-butyl, pentyl, or hexyl, each of which is optionally substituted with hydroxy. In several additional examples, $R_2$ is methyl or ethyl, each of which is substituted with hydroxy.

In several embodiments, $R'_2$ is H. In some embodiments, $R_2$ and $R'_2$ together form oxo.

In some embodiments, when one of $R_1$ or $R_4$ is H, the other is not ethyl.

In several embodiments, the composition further comprises a pharmaceutically acceptable carrier.

Another aspect of the present invention provides a pharmaceutical composition include a compound of formula II:

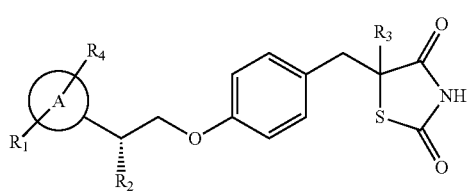

II or a pharmaceutically acceptable salt thereof, wherein $R'_2$ is H, and $R_1$, $R_3$, $R_4$ and ring A are defined above in formula I.

Exemplary compositions according to the present invention includes a single unit dosage form having about 1 mg to about 200 mg of a compound of formulae I or II, e.g., between about 10 mg to about 120 mg, between about 10 mg to about 100 mg, or about 15 mg to about 60 mg.

Several exemplary compounds of formulae I or II are displayed in Table A, below.

TABLE A

Exemplary compounds.

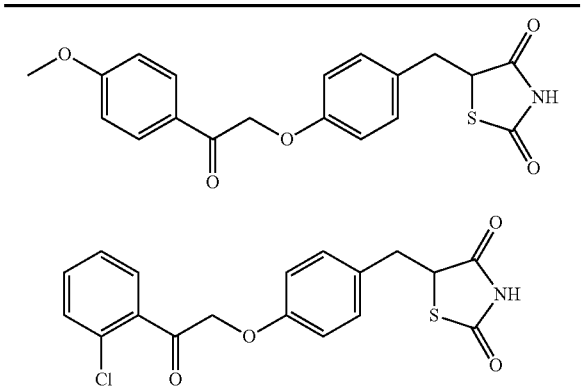

TABLE A-continued

Exemplary compounds.

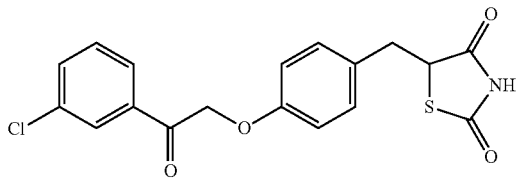
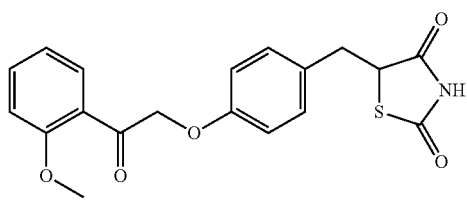
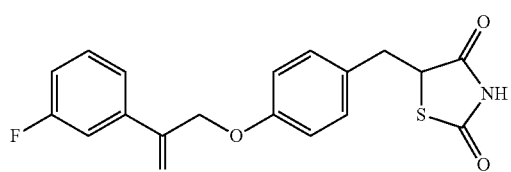
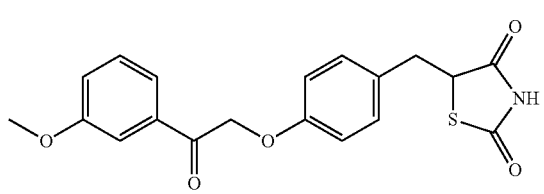
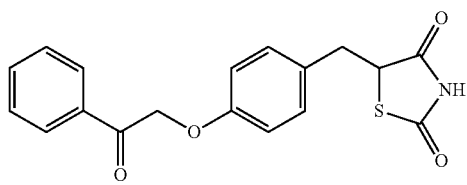
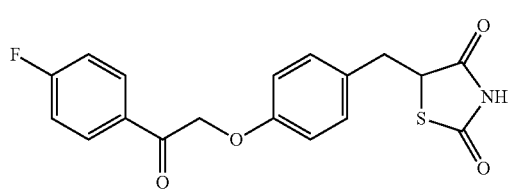
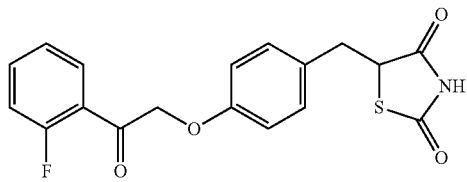

Another aspect of the present invention provides a pharmaceutical composition comprising a compound of formulae I or II, wherein the compound has a PPARγ activity of 50% or less relative to the activity of rosiglitazone when dosed to produce circulating levels greater than 3 μM or having a PPARγ activity of 10 times less than pioglitazone at the same dosage.

Another aspect of the present invention provides a method of treating hypertension, diabetes, and inflammatory diseases comprising administering a pharmaceutical composition comprising a compound of formulae I or II. The compositions of several alternative methods further comprise a pharmaceutically acceptable carrier.

Another aspect of the present invention provides a method of treating hypertension, diabetes, and inflammatory diseases comprising administering a pharmaceutical composition comprising a compound of formula II wherein said compound has a purity of about 70 e.e. % or more. For example, the method treating hypertension, diabetes, and inflammatory diseases comprising administering a pharmaceutical composition comprising a compound of formula I wherein the compound has a purity of about 80% e.e. or more (e.g., 90% e.e. or more, 95% e.e. or more, 97% e.e. or more, or 99% e.e. or more).

Pharmaceutical compositions of the present invention can also comprise one or more additional antihypertensive agents or other drugs. One aspect of the present invention provides pharmaceutical composition comprising a compound of formulae I or II and at least one diuretic, such as hydrochlorothiazide, chlorothaladone, chlorothiazide, or combinations thereof. Other aspects provide pharmaceutical compositions useful for treating hypertension, diabetes, and inflammatory diseases comprising a compound of formulae I or II and one or more agents that limit the activity of the renin-angiotensin system such as angiotensin concerting enzyme inhibitors, i.e. ACE inhibitors, e.g. ramipril, captopril, enalapril, or the like, and/or angiotensin II receptor blockers, i.e. ARBs, e.g. candesartan, losartan, olmesartan, or the like; and/or renin inhibitors. Still other aspects provide a useful pharmaceutical composition for treating hypertension, diabetes, and inflammatory diseases comprising of a compound of formulae I or II and compounds that limit hypertension, diabetes, and inflammatory diseases by alternate means including β-adrenergic receptor blockers, and calcium channel blockers, e.g., amlodipine.

This invention also provides pharmaceutical compositions that are useful for lowering lipids comprising compounds of formulae I or II and one or more statin, i.e., HMG-CoA reductase inhibitor, e.g., atorvastatin, cerivastatin, fluvastatin, lovastatin, mevastatin, simvastatin, rosuvastatin, pravastatin, or any pharmaceutically acceptable combination thereof.

Another aspect of the present invention provides a combination of a compound of formulae I or II with one or more antihypertensive agents including diuretics (for example hydrochlorothiazide, chlorothaladone, chlorothiazide), angiotensive converting enzyme inhibitors, e.g., ACE inhibitors, e.g., ramipril, captopril, enalapril, combinations thereof, or the like; angiotensin II receptor blockers, i.e., ARBs, e.g., losartan, olmesartan, telmisartan, combinations thereof, or the like; renin inhibitors; β-adrenergic receptor blockers, statins, or combinations thereof.

III. General Synthetic Schemes

The compounds of formulae I and II may be readily synthesized from commercially available or known starting materials by known methods. Exemplary synthetic routes to produce compounds of formulae I or II are provided below in Scheme 1 below.

Scheme 1:

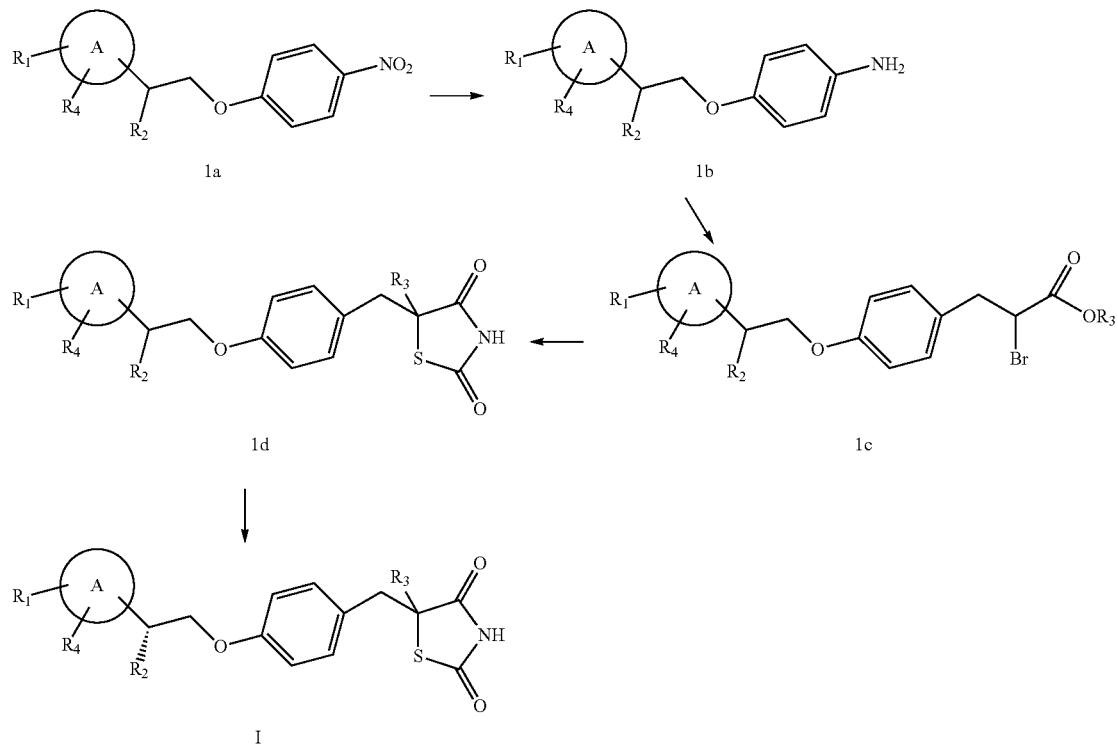

Referring to Scheme 1, the starting material 1a is reduced to form the aniline 1b. The aniline 1b is diazotized in the presence of hydrobromic acid, acrylic acid ester, and a catalyst such as cuprous oxide to produce the alpha-bromo acid ester 1c. The alpha-bromo acid ester 1c is cyclized with thiourea to produce racemic thiazolidinedione 1d. Compounds of formula II can be separated from the racemic mixture using any suitable process such as HPLC.

In Scheme 2 below, $R_2$ is an oxo group, $R_3$ is hydrogen.

Scheme 2:

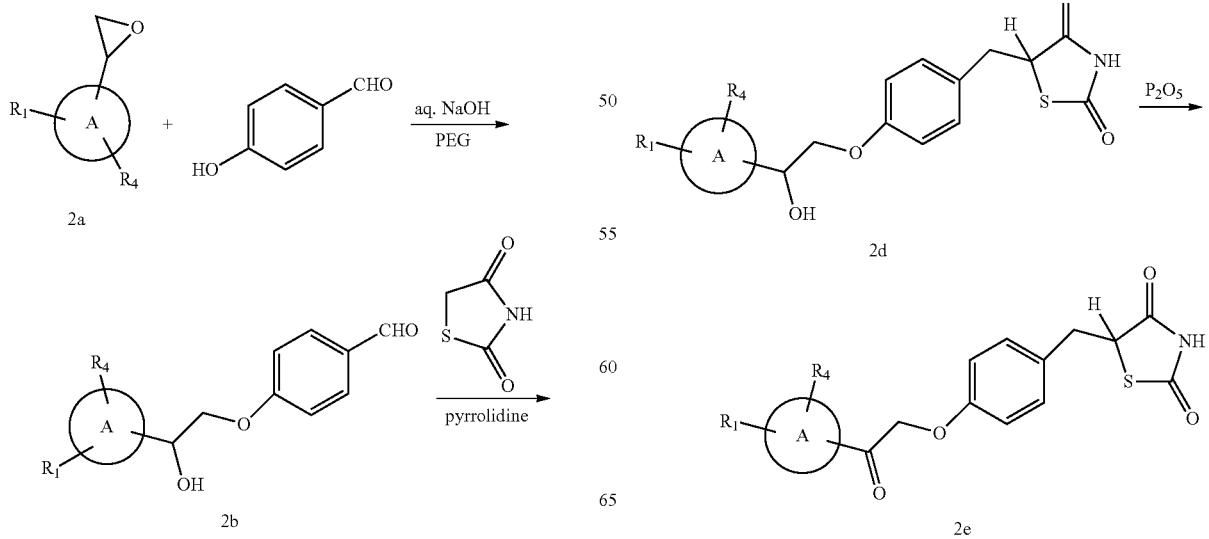

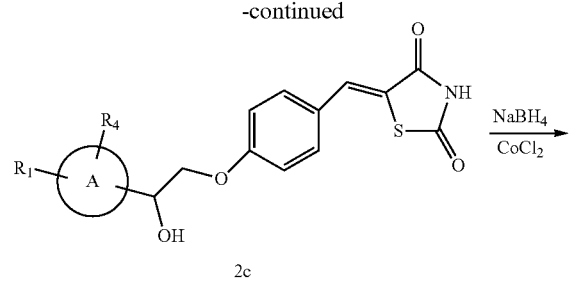

Referring to Scheme 2, the starting material 2a is reacted with 4-hydroxybenzalde under basic conditions (e.g., aq. NaOH) to give a mixture of regioisomeric alcohols 2b that were separated by chromatography. The regioisomeric alcohols 2b is reacted with 2,4-thiazolidine dione using pyrrolidine as base to give compound 2c. Cobalt catalyzed reduction with sodium borohydride affords compound 2d, which is oxidized, for example, with phosphorus pentoxide in the presence of dimethyl sulfoxide, to give the ketone 2e.

IV. Uses, Formulations, and Administration

As discussed above, the present invention provides compounds that are useful as treatments for hypertension, diabetes, and inflammatory diseases.

Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative or a prodrug thereof. According to the present invention, a pharmaceutically acceptable derivative or a prodrug includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof.

Pharmaceutically acceptable salts are well known in the art. For example, S. M. Berge, et al. describes pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersible products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In yet another aspect, the present invention provides a method of treating hypertension, diabetes, and inflammatory diseases comprising administering a pharmaceutical composition comprising a compound of formulae I or II, preferably a mammal, in need thereof.

According to the invention an "effective amount" of the compound or pharmaceutically acceptable composition is that amount effective for treating or lessening the severity of hypertension, diabetes, and inflammatory diseases.

The pharmaceutical compositions, according to the method of the present invention, may be administered using any amount and any route of administration effective for treating or lessening the severity of hypertension, diabetes, and inflammatory diseases.

The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors known in the medical arts. The term "patient", as used herein, means an animal, for example, a mammal, and more specifically a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect. Alternatively, the compounds of the invention may be administered orally or parenterally at dosage levels of between 10 mg/kg and about 120 mg/kg.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsulated matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as treatments for hypertension, diabetes, and inflammatory diseases.

The activity, or more importantly, reduced PPARγ activity of a compound utilized in this invention as a treatment of hypertension, diabetes, and inflammatory diseases may be assayed according to methods described generally in the art and in the examples herein.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121, each of which is incorporated by reference. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

According to yet another embodiment, the present invention provides a method of treating or reducing the severity of hypertension, diabetes, and inflammatory diseases.

Another aspect of the invention relates to treating hypertension, diabetes, and inflammatory diseases in a biological sample or a patient (e.g., in vitro or in vivo), which method comprises administering to the patient, or contacting said biological sample with a pharmaceutical composition comprising a compound of formulae I or II. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

In order that the invention described herein may be more fully understood, the following examples are set forth. It should be understood that these examples are for illustrative purposes only and are not to be construed as limiting this invention in any manner.

V. EXAMPLES

Example 1

5-[4-(2-oxo-2-phenylethoxy)benzyl]-1,3-thiazolidine-2,4-dione

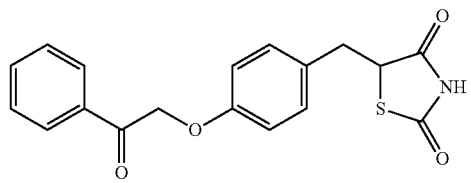

Step 1. Preparation of 4-(2-hydroxy-2-phenylethoxy)benzaldehyde.

To 2-(4-fluorophenyl)oxirane (6.50 g, 54.0 mmol) was added toluene (85 ml), 4-hydroxybenzaldehyde (9.89 g, 81.0 mmol), PEG4000 (polyethylene glycol, 1.15 g) and 1M NaOH (85 ml) and the stirring mixture was heated at 78° C. overnight. After cooling to RT the reaction mixture was extracted with EtOAc, and the organic phase was washed with brine, dried ($Na_2SO_4$), filtered and evaporated in vacuo. The resulting yellow oil was chromatographed on a medium silica gel column eluting with 0-10% EtOAc/DCM. Fractions containing predominantly the higher $R_f$ spot were combined and evaporated in vacuo to give 1.85 g (14%) of the title compound as a yellow oil. Fractions containing predominantly the lower $R_f$ spot were combined and evaporated in vacuo to give 0.64 g of the regioisomer as a colorless, viscous oil. Mixed fractions were combined and rechromatographed eluting with 30% EtOAc/hexanes. Fractions containing the higher $R_f$ material were combined and evaporated in vacuo to give an additional 2.64 g (20%) of the title compound as a colorless oil. Fractions containing the lower $R_f$ material were combined and evaporated in vacuo to give an additional 1.82 g of the regioisomer as a colorless viscous oil.

Step 2: Preparation of 5-[4-(2-hydroxy-2-phenylethoxy)benzylidene]-1,3-thiazolidine-2,4-dione.

To a stirring solution of 4-[(2S)-2-hydroxy-2-phenylethoxy]benzaldehyde (2.63 g, 10.8 mmol) in absolute EtOH (75 ml) was added 2,4-thiazolidinedione (1.27 g, 10.8 mmol) and piperidine (0.54 mL, 5.4 mmol), and the resulting solution was heated to reflux. The reaction was refluxed overnight. The reaction mixture was allowed to cool to RT. No precipitate formed. The pH of reaction mixture was ca. 5. Acetic acid (20 drops) was added. The reaction was evaporated in vacuo. The material was adsorbed onto silica gel and chromatographed eluting with 30-40% EtOAc/hexanes. Fractions containing product were combined and evaporated in vacuo to give 3.18 g (86%) of the title compound as a light yellow solid. MS (ESI–) for $C_{18}H_{15}NO_4S$ m/z 340.1 (M–H)⁻.

Step 3: Preparation of 5-[4-(2-hydroxy-2-phenylethoxy)benzyl]-1,3-thiazolidine-2,4-dione.

To a mixture of 5-[4-(2-hydroxy-2-phenylethoxy)benzylidene]-1,3-thiazolidine-2,4-dione (1.50 g, 4.39 mmol) in THF (20 ml) was added $H_2O$ (20 ml), 1M NaOH (3 ml), cobalt (II) chloride hexahydrate (0.60 mg, 0.003 mmol) and dimethylglyoxime (15 mg, 0.13 mmol). A solution of sodium tetrahydroborate (240 mg, 6.33 mmol) in 0.2M NaOH (3.6 ml) was added. The reaction mixture immediately turned dark but very soon assumed a clear yellow appearance. Acetic acid was added dropwise until the solution turned dark (3 drops). After ca. one hour the reaction lightened. Additional $NaBH_4$, $CoCl_2$ and HOAc were added to produce a deep blue-purple color. When that color faded, more $NaBH_4$ was added. When HPLC analysis indicated that the reaction was complete, it was partitioned between $H_2O$ and EtOAc, and the organic phase was washed with brine, dried ($Na_2SO_4$), filtered and evaporated in vacuo. The resulting foamy solid was chromatographed, eluting with 50% EtOAc/hexanes. Fractions containing product were combined and evaporated in vacuo to give 1.15 g (76%) of the title compound as a white solid. MS (ESI–) for $C_{18}H_{17}NO_4S$ m/z 342.1 (M–H)⁻.

Step 4: Preparation of 5-[4-(2-oxo-2-phenylethoxy)benzyl]-1,3-thiazolidine-2,4-dione To a stirring solution of 5-[4-(2-hydroxy-2-phenylethoxy)benzyl]-1,3-thiazolidine-2,4-dione (1.00 g, 2.91 mmol) in DCM (35 ml) was added DMSO (2 ml) and the solution was cooled to 0° C. Phosphorus pentoxide (0.83 g, 2.91 mmol) was added followed by triethylamine (1.8 mL, 13.1 mmol). The reaction was allowed to slowly warm to RT. After 2 hours, the reaction mixture was partitioned between DCM and water and the organic phase was washed with brine, dried ($Na_2SO_4$), filtered and evaporated in vacuo. The resulting yellow oil was chromatographed on silica gel eluting with 25-35% EtOAc/hexanes. Fractions containing product were combined and evaporated in vacuo to give 0.40 g (40%) of the title compound as a white solid. Trituration with ether afforded 245 mg of clean product. MS (ESI–) for $C_{18}H_{15}NO_4S$ m/z 340.1 (M–H)⁻

Example 2

Preparation of 5-{4-[2-(4-fluorophenyl)-2-oxoethoxy]benzyl}-1,3-thiazolidine-2,4-dione

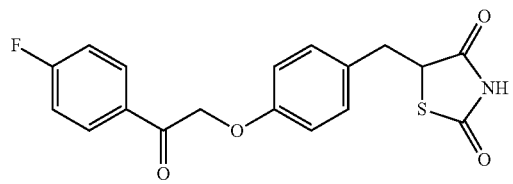

Step 1: Preparation of 4-[2-(fluorophenyl)-2-hydroxyethoxy]benzaldehyde.

To a stirring solution of 2-(4-fluorophenyl)oxirane (5.60 g, 40.0 mmol) in toluene (65 ml) was added 4-hydroxybenzaldehyde (7.40 g, 61.0 mmol), 1M NaOH (65 ml) and PEG4000 (polyethylene glycol, 0.85 g) and the reaction was heated at 78° C. overnight. After cooling to RT, the reaction was extracted with EtOAc (2×150 ml) and the combined extracts were washed with brine, dried ($Na_2SO_4$), filtered and evaporated in vacuo. The resulting light brown oil was chromatographed on silica gel eluting with 30-40% EtOAc/hexanes. Fractions containing the higher $R_f$ spot were combined and evaporated in vacuo to give 2.38 g of the regioisomer of the product as a white solid. Fractions containing the lower Rf spot were combined and evaporated in vacuo to give 1.54 g (22%) of the title compound as a colorless viscous oil.

Step 2: Preparation of 5-{4-[2-(4-fluorophenyl)-2-hydroxyethoxy]benzylidene}-1,3-thiazolidine-2,4-dione To a stirring solution of the aldehyde (2.36 g, 10.8 mmol) in absolute EtOH (75 ml) was added 2,4-thiazolidinedione (1.06 g, 9.07 mmol) and piperidine (0.45 mL, 4.50 mmol), and the resulting solution was heated to reflux. After refluxing overnight, the reaction was allowed to cool to RT, and then evaporated in vacuo. The residue was adsorbed onto silica gel and chromatographed, eluting with 30-40% EtOAc/hexanes. Fractions containing product were combined and evaporated in vacuo to give 0.88 g (27%) of the title compound as a yellow solid. MS (ESI−) for $C_{18}H_{14}FNO_4S$ m/z 358.1 (M−H)−.

Step 3: Preparation of 5-{4-[2-(4-fluorophenyl)-2-hydroxyethoxy]benzyl}-1,3-thiazolidine-2,4-dione To a stirring mixture of 5-{4-[2-(4-fluorophenyl)-2-hydroxyethoxy]benzylidene}-1,3-thiazolidine-2,4-dione (0.87 g, 2.40 mmol) in THF/$H_2O$ (1:1, 20 ml) was added 1M NaOH (2 ml), cobalt (II) chloride hexahydrate (0.30 g, 0.001 mmol), dimethylglyoxime (8.4 mg, 0.073 mmol), and finally sodium tetrahydroborate (0.13 g, 3.53 mmol). The reaction turned a deep blue/purple color. After a short time, the dark color began to fade and HOAc was added dropwise to regenerate the darker color. When the color faded and addition of HOAc failed to regenerate it, NaBH$_4$ was added to regenerate the darker color. The reaction was left to stir at RT overnight. The reaction was partitioned between water and EtOAc. The organic phase was washed with brine, dried (Na$_2$SO$_4$), filtered and evaporated in vacuo. The resulting light brown oil was chromatographed, eluting with 35% EtOAc/hexanes. Fractions containing compound were combined and evaporated in vacuo to give 0.77 g (88%) of a light yellow solid. The yellow solid was dissolved in THF (8 ml) and H$_2$O (8 ml), and the resulting solution was treated with CoCl$_2$ (a small crystal), and 2,2'-dipyridyl (5 mg). Finally, NaBH$_4$ was added in small portions until the deep blue color persisted. The reaction mixture was partitioned between EtOAc and H$_2$O, and the aqueous phase was extracted with EtOAc. The combined organic phases were washed with brine, dried (Na$_2$SO$_4$), filtered and evaporated in vacuo. The resulting slightly tinted oil was chromatographed on a small silica gel column eluting with 25-35% EtOAc/hexanes. Fractions containing product were combined and evaporated in vacuo to afford 527 mg (60%) of the title compound as a white solid. MS (ESI−) for $C_{18}H_{16}FNO_4S$ m/z 360.1 (M−H)−.

Step 4: Preparation of 5-{4-[2-(4-fluorophenyl)-2-oxoethoxy]benzyl}-1,3-thiazolidine-2,4-dione To a stirring solution of 5-{4-[2-(4-fluorophenyl)-2-hydroxyethoxy]benzyl}-1,3-thiazolidine-2,4-dione (0.52 g, 1.40 mmol) in DCM (15 ml) was added DMSO (0.5 ml) and the solution was cooled to 0° C. Phosphorus pentoxide (0.41 g, 1.44 mmol) was added followed by triethylamine (0.90 mL, 6.48 mmol). The reaction was allowed to slowly warm to RT and then stirred for 5 hours. The reaction mixture was partitioned between DCM and H$_2$O, and the aqueous phase was extracted with DCM. The combined organic phases were washed with brine, dried (Na$_2$SO$_4$), filtered and evaporated in vacuo. The resulting white solid was chromatographed on a small silica gel column eluting with 10% EtOAc/DCM. Fractions containing product were combined and evaporated in vacuo to give 0.25 g (48%) of the title compound as a white solid. MS (ESI+) for $C_{18}H_{14}FNO_4S$ m/z 359.9 (M+H)+. MS (ESI−) for $C_{18}H_{14}FNO_4S$ m/z 358.0 (M−H)−.

Example 3

Preparation of 5-{4-[2-(2-fluorophenyl)-2-oxoethoxy]benzyl}-1,3-thiazolidine-2,4-dione

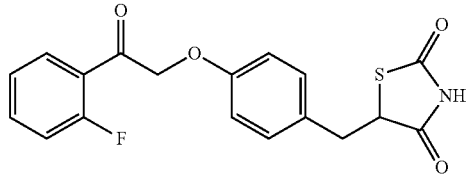

Step 1: Preparation of 2-(2-fluorophenyl)oxirane.

To a solution of o-fluorostyrene (5.0 g, 41.0 mmol) and acetic acid (2.33 mL, 40.9 mmol) in dioxane (33 ml) and H$_2$O (78 ml) at 0° C. was added N-bromosuccinimide (8.02 g, 45.0 mol) in three portions. The reaction was allowed to warm to R.T and stirred overnight. Sodium carbonate (8.68 g, 81.9 mmol) was added in portions and then 1M NaOH (ca. 10 ml) was added and the reaction was stirred at RT overnight. The reaction mixture was partitioned between water and EtOAc, and the aqueous phase was extracted with EtOAc. The combined organic phases washed with brine, dried (Na$_2$SO$_4$), filtered and evaporated in vacuo to give 5.31 g (94%) of the title compound as a slightly tinted oil which was used without further purification. MS (ESI+) for $C_8H_7FO$ m/z 138.1 (M+H)+.

Step 2: Preparation of 4-[2-(2-fluorophenyl)-2-hydroxyethoxy]benzaldehyde.

To a stirring solution of 2-(2-fluorophenyl)oxirane (5.30 g, 38.4 mmol) in toluene (65 ml) was added 4-hydroxybenzaldehyde (7.0 g, 58.0 mmol), 1M NaOH (65 ml) and PEG4000 (polyethylene glycol, 0.85 g) and the stirring mixture was heated at 78° C. overnight. The reaction was allowed to cool to RT and then extracted with EtOAc (2×150 ml). The combined extracts were washed with brine, dried (Na$_2$SO$_4$), filtered and evaporated in vacuo. The resulting light brown oil was adsorbed onto silica gel and chromatographed, eluting with 30-40% EtOAc/hexanes. There are 2 major spots. Fractions containing the higher $R_f$ spot were combined and evaporated in vacuo to give 1.10 g (11%) of the title compound as a colorless oil. Fractions containing the lower $R_f$ spot were combined and evaporated in vacuo to give 0.67 g (7%) of the regioisomer as a colorless oil.

Step 3: Preparation of 5-{4-[2-(2-fluorophenyl)-2-hydroxyethoxy]benzylidene}-1,3-thiazolidine-2,4-dione.

To a stirring solution of the aldehyde (2.36 g, 10.8 mmol) in absolute EtOH (40 ml) was added 2,4-thiazolidinedione (0.495 g, 4.23 mmol) and piperidine (0.21 mL, 2.10 mmol), and the resulting solution was heated to reflux. After refluxing overnight, the reaction mixture was cooled to RT and then evaporated in vacuo. The residue was dissolved in EtOAc and this solution was washed with dilute aqueous HOAc, brine, dried (Na$_2$SO$_4$), filtered and evaporated in vacuo. The resulting yellow solid was washed with DCM and acetone and the filtrate was evaporated in vacuo. This material was adsorbed onto silica gel and chromatographed using 10-25% EtOAc/DCM. Fractions containing compound were combined and evaporated in vacuo to give 0.51 g of the title compound as a yellow solid. MS (ESI–) for $C_{18}H_{14}FNO_4S$ m/z 358.0 (M–H)⁻.

Step 4: Preparation of 5-{4-[2-(2-fluorophenyl)-2-hydroxyethoxy]benzyl}-1,3-thiazolidine-2,4-dione.

To a stirring mixture of 5-{4-[2-(2-fluorophenyl)-2-hydroxyethoxy]benzylidene}-1,3-thiazolidine-2,4-dione (0.52 g, 1.40 mmol) in THF/H₂O (1:1, 16 ml) was added 1M NaOH (2 ml), cobalt (II) chloride hexahydrate (0.2 mg, 0.0009 mmol), 2,2'-bipyridine (50.8 mg, 0.33 mmol), and finally sodium tetrahydroborate (0.11 g, 2.90 mmol). The reaction turned a deep blue/purple color. After a short time, the dark color began to fade and HOAc was added dropwise to regenerate the darker color. When the color faded and addition of HOAc failed to regenerate it, NaBH₄ was added to regenerate the darker color. Added small portions of NaBH₄ and HOAc dropwise until deep blue color persisted. After repeating this several times, HPLC indicated that the reaction was complete despite the fact that the deep blue color has given way to a light brown solution. The reaction was partitioned between water and EtOAc. The organic phase was washed with brine, dried (Na₂SO₄), filtered and evaporated in vacuo. The resulting light brown oil was chromatographed, eluting with 35% EtOAc/hexanes. Fractions containing compound were combined and evaporated in vacuo to give 0.32 g of the title compound as a white solid. MS (ESI–) for $C_{18}H_{16}FNO_4S$ m/z 360.1 (M–H)⁻.

Step 5: Preparation of 5-{4-[2-(2-fluorophenyl)-2-oxoethoxy]benzyl}-1,3-thiazolidine-2,4-dione To a stirring solution of 5-{4-[2-(2-fluorophenyl)-2-hydroxyethoxy]benzyl}-1,3-thiazolidine-2,4-dione (0.29 g, 0.80 mmol) in DCM (15 ml) was added DMSO (0.5 ml) and the solution was cooled to 0° C. Phosphorus pentoxide (0.23 g, 0.80 mmol) was added, followed by triethylamine (0.50 mL, 3.6 mmol). The reaction was allowed to slowly warm to RT. After 3 hours, water was added and the phases were separated. The pH of the aqueous phase was adjusted to ca. 7 and the aqueous phase was extracted with DCM. The combined organic phases were washed with brine, dried (Na₂SO₄), filtered and evaporated in vacuo. The resulting white solid was chromatographed on a small silica gel column eluting with 10% EtOAc/DCM. Fractions containing product were combined and evaporated in vacuo to give 0.19 g (66%) of the title compound as a white solid. MS (ESI–) for $C_{18}H_{14}FNO_4S$ m/z 358.0 (M–H)⁻.

Example 4

Preparation of 5-{4-[2-(3-fluorophenyl)-2-oxoethoxy]benzyl}-1,3-thiazolidine-2,4-dione

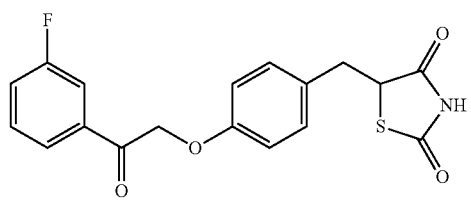

Step 1: Preparation of 2-(3-fluorophenyl)oxirane.

To a solution of m-fluorostyrene (5.00 g, 41.0 mmol) and acetic acid (2.33 mL, 40.9 mmol) in dioxane (33 ml) and H₂O (78 ml) at 0° C. was added N-bromosuccinimide (8.02 g, 45.0 mmol) in three portions. The reaction was allowed to warm to RT. After 4 hours, 2N NaOH (60 ml) was added and the reaction was left to stir at RT overnight. The reaction mixture was partitioned between water and EtOAc, and the aqueous phase was extracted with EtOAc. The combined organic phases were washed with brine, dried (Na₂SO₄), filtered and evaporated in vacuo to give 6.30 g of the title compound as a slightly tinted oil which was used without further purification.

Step 2: Preparation of 4-[2-(3-fluorophenyl)-2-hydroxyethoxy]benzaldehyde.

To a stirring solution of 2-(3-fluorophenyl)oxirane (5.60 g, 40.5 mmol) in toluene (65 ml) was added 4-hydroxybenzaldehyde (7.40 g, 61.0 mmol), 1M NaOH (65 ml) and PEG4000 (polyethylene glycol, 0.85 g) and the stirring mixture was heated at 78° C. overnight. The reaction mixture was allowed to cool to RT and then extracted with EtOAc (2×150 ml). The combined extracts were washed with brine, dried (Na₂SO₄), filtered and evaporated in vacuo. The resulting light brown oil was chromatographed eluting with 30-40% EtOAc/hexanes. There are 2 major spots. Fractions containing the higher $R_f$ spot were combined and evaporated in vacuo to give 1.78 g (17%) of the title compound as a white solid. Fractions containing the lower $R_f$ spot were combined and evaporated in vacuo to give 0.90 g (9%) of the regioisomer as a nearly colorless oil.

Step 3: Preparation of 5-{4-[2-(3-fluorophenyl)-2-hydroxyethoxy]benzylidene}-1,3-thiazolidine-2,4-dione.

To a stirring solution of the aldehyde (2.36 g, 10.8 mmol) in absolute EtOH (40 ml) was added 2,4-thiazolidinedione (0.90 g, 7.69 mmol) and piperidine (0.76 mL, 7.7 mmol), and the resulting solution was heated to reflux. After 6 hours, the reaction mixture was allowed to cool to RT. The mixture was evaporated in vacuo and the residue was dissolved in EtOAc. This solution was washed with a dilute aqueous HOAc, brine, dried (Na₂SO₄), filtered and evaporated in vacuo. The resulting yellow solid was dissolved in MeOH/DCM adsorbed onto silica gel and chromatographed eluting with 30% EtOAc/DCM. Fractions containing compound were combined and evaporated in vacuo to afford 2.17 g (86%) of the title compound as a yellow solid. MS (ESI–) for $C_{18}H_{14}FNO_4S$ m/z 358.1 (M–H)⁻.

Step 4: Preparation of 5-{4-[2-(3-fluorophenyl)-2-hydroxyethoxy]benzyl}-1,3-thiazolidine-2,4-dione.

5-{4-[2-(3-fluorophenyl)-2-hydroxyethoxy]benzylidene}-1,3-thiazolidine-2,4-dione (1.00 g, 2.78 mmol) was suspended in THF (15 ml) and H₂O (10 ml). To this solution was added a small crystal of cobalt chloride followed by 2,2'-bipyridine (98 mg, 0.63 mmol). NaBH₄ was added in portions until blue color persisted. The color gradually faded and was regenerated repeatedly by small additions of borohydride and HOAc. When HPLC analysis indicated that the reaction was complete, the reaction mixture was partitioned between EtOAc and H₂O. HOAc was added until the pH of the aqueous phase was ca. 6. The aqueous phase was extracted with EtOAc. The combined organic phases were washed with brine, dried (Na₂SO₄), filtered and evaporated in vacuo. The residue was chromatographed on a small silica gel column eluting with 20% EtOAc/DCM. Fractions containing product were combined and evaporated in vacuo to give 0.72 g (72%) of the title compound as a white solid. This material was rechromatographed on a small silica column eluting with 10-20% EtOAc/DCM. MS (ESI–) for $C_8H_{16}FNO_4S$ m/z 360.1 (M–H)⁻.

Step 5: Preparation of 5-{4-[2-(3-fluorophenyl)-2-oxoethoxy]benzyl}-1,3-thiazolidine-2,4-dione.

To a stirring solution of 5-{4-[2-(3-fluorophenyl)-2-hydroxyethoxy]benzyl}-1,3-thiazolidine-2,4-dione (0.62 g, 1.70 mmol) in DCM (15 ml) was added DMSO (0.5 ml) and the solution was cooled to 0° C. Added phosphorus pentoxide (0.49 g, 1.72 mmol) followed by triethylamine (1.1 mL, 7.72 mmol). The reaction mixture was allowed to slowly warm to RT. After 2 hours, HPLC shows that the reaction was complete. Added water and separated phases. The pH of the aqueous phase was adjusted to ca. 7 with 2M NaOH and the aqueous phase was then extracted with EtOAc. The combined extracts were washed with brine, dried ($Na_2SO_4$), filtered and evaporated in vacuo. The resulting white solid was chromatographed on a small silica gel column eluting with 10% EtOAc/DCM. Fractions containing product were combined and evaporated in vacuo to give 0.25 g (40%) of the title compound as a white solid. MS (ESI−) for $C_{18}H_{14}FNO_4S$ m/z 358.0 (M−H)⁻.

Example 5

Preparation of 5-{4-[2-(3-methoxyphenyl)-2-oxoethoxy]benzyl}-1,3-thiazolidine-2,4-dione

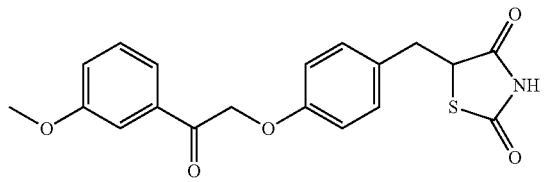

Step 1: 2-(3-methoxyphenyl)oxirane.

To a solution of 3-vinylanisole (5.0 g, 37.0 mmol) and acetic acid (2.1 mL, 37.0 mmol) in dioxane (33 ml) and $H_2O$ (78 ml) at 0° C. was added N-bromosuccinimide (7.30 g, 41.0 mmol) in three portions. The reaction was allowed to warm to R.T. and then 2M NaOH (50 ml) was added. The reaction was left to stir at RT overnight. The reaction mixture was then partitioned between water and EtOAc, and the aqueous phase was extracted with EtOAc. The combined organic phases washed with brine, dried ($Na_2SO_4$), filtered and evaporated in vacuo to give 5.60 g (100%) of the title compound as a slightly tinted oil.

Step 2: 4-[2-hydroxy-2-(3-methoxyphenyl)ethoxy]benzaldehyde

To a stirring solution of 2-(3-methoxyphenyl)oxirane (5.60 g, 37.0 mmol) in toluene (65 ml) was added 4-hydroxybenzaldehyde (6.80 g, 5.60 mmol), 1M NaOH (65 ml) and PEG4000 (polyethylene glycol, 0.85 g) and the stirring mixture was heated at 78° C. overnight. The reaction mixture was allowed to cool to RT and extracted with EtOAc (2×150 ml). The combined extracts were washed with brine, dried ($Na_2SO_4$), filtered and evaporated in vacuo. The resulting light brown oil was chromatographed, eluting with 30-40% EtOAc/hexanes. Fractions containing the higher $R_f$ spot were combined and evaporated in vacuo to give 1.86 g (18%) of the title compound as a clear colorless oil. Fractions containing the lower $R_f$ spot were combined and evaporated in vacuo to give 0.90 g (9%) the regioisomer as a nearly colorless oil.

Step 3: 5-{4-[2-hydroxy-2-(3-methoxyphenyl)ethoxy]benzylidene}-1,3-thiazolidine-2,4-dione.

To a stirring solution of 4-[2-hydroxy-2-(3-methoxyphenyl)ethoxy]benzaldehyde (1.76 g, 6.46 mmol) in absolute EtOH (50 ml) was added 2,4-thiazolidinedione (0.83 g, 7.11 mmol) and piperidine (0.70 mL, 7.11 mmol), and the resulting solution was heated to reflux. The reaction was refluxed overnight and then evaporated in vacuo. The residue was dissolved in EtOAc and this solution was washed with water (pH adjusted to ca. 5-6 with HOAc), brine, dried ($Na_2SO_4$), filtered and adsorbed onto silica gel. After chromatography with 20-30% EtOAc/DCM, the fractions containing compound were combined and evaporated in vacuo to give 1.38 g (58%) of the title compound as a yellow solid. MS (ESI−) for $C_{19}H_{17}NO_5$ m/z 370.1 (M−H)⁻.

Step 4: 5-{4-[2-hydroxy-2-(3-methoxyphenyl)ethoxy]benzyl}-1,3-thiazolidine-2,4-dione.

5-{4-[2-hydroxy-2-(3-methoxyphenyl)ethoxy]benzylidene}-1,3-thiazolidine-2,4-dione (1.15 g, 3.10 mmol) was dissolved in THF (15 ml). Added $H_2O$ (15 ml) and sufficient THF to give a clear solution. A small crystal of cobalt chloride was added, followed by 2,2'-bipyridine (109 mg, 0.70 mmol). $NaBH_4$ was added in portions until the blue color persisted. The color gradually faded, but was regenerated repeatedly by small additions of borohydride and HOAc. When HPLC indicated that the reaction was complete the reaction mixture was partitioned between EtOAc and $H_2O$. HOAc was added until the pH of the aqueous phase was ca. 6, and then the aqueous phase was extracted with EtOAc. The combined organic phases were washed with brine, dried ($Na_2SO_4$), filtered and evaporated in vacuo. The residue was chromatographed on a small silica gel column eluting with 20% EtOAc/DCM. Fractions containing product were combined and evaporated in vacuo to give 0.82 g (74%) of the title compound as a white solid. MS (ESI−) for $C_{19}H_{19}NO_5S$ m/z 372.0 (M−H)⁻.

Step 5: Preparation of 5-{4-[2-(3-methoxyphenyl)-2-oxoethoxy]benzyl}-1,3-thiazolidine-2,4-dione To a stirring solution of 5-{4-[2-hydroxy-2-(3-methoxyphenyl)ethoxy]benzyl}-1,3-thiazolidine-2,4-dione (0.62 g, 1.7 mmol) in DCM (15 ml) was added DMSO (0.5 ml) and the solution was cooled to 0° C. Added phosphorus pentoxide (0.52 g, 1.8 mmol) followed by triethylamine (1.2 mL, 8.3 mmol). The reaction was allowed to slowly warm to RT. After 2 hours water was added and the phases were separated. The pH of the aqueous phase was adjusted to ca. 7 with 2M NaOH. The aqueous phase was extracted with EtOAc. The combined extracts were washed with brine, dried ($Na_2SO_4$), filtered and evaporated in vacuo. The resulting white solid was chromatographed on a small silica gel column eluting with 10% EtOAc/DCM. Fractions containing product were combined and evaporated in vacuo to give 0.33 g (54%) of the title compound as a white solid. MS (ESI+) for $C_{19}H_{17}NO_5S$ m/z 372.0 (M+H)⁺. MS (ESI−) for $C_{19}H_{17}NO_5S$ m/z 370.1 (M−H)⁻.

Example 6

Preparation of 5-{4-[2-(2-methoxyphenyl)-2-oxoethoxy]benzyl}-1,3-thiazolidine-2,4-dione

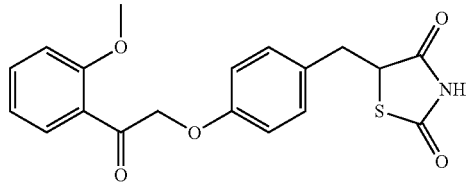

Step 1: Preparation of 2-(2-methoxyphenyl)oxirane.

To a solution of 2-vinyl anisole (5.0 g, 0.037 mol) and acetic acid (2.1 mL, 37 mmol) in dioxane (33 ml) and $H_2O$ (78 ml) at 0° C. was added N-bromosuccinimide (7.30 g, 40.1 mmol) in three portions. The reaction was allowed to warm to R.T. and after 1 hour, 2M NaOH (50 ml) was added. The reaction was left to stir at RT overnight. The reaction mixture was partitioned between water and EtOAc, and the aqueous phase was extracted with EtOAc. The combined organic phases were washed with brine, dried ($Na_2SO_4$), filtered and evaporated in vacuo to give 7.56 g slightly tinted oil. This was dissolved in dioxane, 2N NaOH was added and the reaction was stirred at RT overnight. Repeated aqueous work-up gave 5.60 g of the title compound as a nearly colorless oil.

Step 2: Preparation of 4-[2-hydroxy-2-(2-methoxyphenyl)ethoxy]benzaldehyde.

To a stirring solution of 2-(2-methoxyphenyl)oxirane (5.60 g, 37.3 mmol) in toluene (65 ml) was added 4-hydroxybenzaldehyde (6.80 g, 56.0 mmol), 1M NaOH (65 ml) and PEG4000 (polyethylene glycol, 0.85 g) and the stirring mixture was heated at 78° C. overnight. The reaction was allowed to cool to RT and it was then extracted with EtOAc (2×150 ml). The combined extracts were washed with brine, dried ($Na_2SO_4$), filtered and evaporated in vacuo. The resulting light oil was adsorbed onto silica gel and chromatographed eluting with 30-40% EtOAc/hexanes. There are 2 major spots. Fractions containing the higher Rf spot were combined and evaporated in vacuo to give 1.71 g (17%) the regioisomer as a brown oil. Fractions containing the lower $R_f$ spot were combined and evaporated in vacuo to give 2.05 g (20%) of the title compound as a yellow solid.

Step 3: Preparation of (5Z)-5-{4-[2-hydroxy-2-(2-methoxyphenyl)ethoxy].benzylidene}-1,3-thiazolidine-2,4-dione To a stirring solution of 4-[2-hydroxy-2-(2-methoxyphenyl)ethoxy]benzaldehyde (1.71 g, 6.28 mmol) in absolute EtOH (50 ml) was added 2,4-thiazolidinedione (0.81 g, 6.91 mmol) and piperidine (0.68 mL, 6.9 mmol), and the resulting solution was heated to reflux. The reaction was refluxed overnight and then evaporated in vacuo. The residue was dissolved in EtOAc and this solution was washed with aqueous HOAc (pH 5-6), brine, dried ($Na_2SO_4$), filtered and evaporated in vacuo. The residue was adsorbed onto silica gel and chromatographed on silica gel eluting with 20-40% EtOAc/DCM. Fractions containing product were combined and evaporated in vacuo to give 1.87 g (80%) of the title compound as a light yellow solid. MS (ESI–) for $C_{19}H_{17}NO_5S$ m/z 370.1 (M–H)⁻.

Step 4: 5-{4-[2-hydroxy-2-(2-methoxyphenyl)ethoxy]benzyl}-1,3-thiazolidine-2,4-dione.

(5Z)-5-{4-[2-hydroxy-2-(2-methoxyphenyl)ethoxy]benzylidene}-1,3-thiazolidine-2,4-dione (1.00 g, 2.69 mmol) was dissolved in THF (20 ml). Water (20 ml) was added and then sufficient additional THF was added to give a clear solution. A small crystal of cobalt chloride was added followed by 2,2'-bipyridine (95 mg, 0.61 mmol). The reaction mixture was cooled to 0° C. NaBH₄ was added in portions until the blue color persisted. The color gradually faded and was regenerated repeatedly by small additions of borohydride and HOAc. When HPLC indicated that the reaction was complete the reaction mixture was partitioned between EtOAc and H₂O. HOAc was added until the pH of the aqueous phase was ca. 6, and the aqueous phase was extracted with EtOAc. The combined organic phases were washed with brine, dried ($Na_2SO_4$), filtered and evaporated in vacuo. The residue was chromatographed on a small silica gel column eluting with 20% EtOAc/DCM. Fractions containing product were combined and evaporated in vacuo to give 0.63 g (63%) of the title compound as a white solid. MS (ESI–) for $C_{19}H_{19}NO_5S$ m/z 372.1 (M–H)⁻.

Step 5: Preparation of 5-{4-[2-(2-methoxyphenyl)-2-oxoethoxy]benzyl}-1,3-thiazolidine-2,4-dione.

To a stirring solution of phosphorus pentoxide (0.30 g, 1.10 mmol) in DCM (8 ml) at 0° C. was added a solution of 5-{4-[2-hydroxy-2-(2-methoxyphenyl)ethoxy]benzyl}-1,3-thiazolidine-2,4-dione (0.20 g, 0.54 mmol) in DCM (8 ml) followed by dimethyl sulfoxide (0.20 mL, 2.80 mmol). After stirring for 15 minutes, N,N-diisopropylethylamine (0.28 mL, 1.60 mmol) was added. After 45 minutes, the reaction mixture was cast into cold saturated NaHCO₃ and extracted with EtOAc (x2). The combined extracts were washed with brine, dried ($Na_2SO_4$), filtered and evaporated in vacuo. The residue was chromatographed on a small silica gel column eluting with 0-10% EtOAc/DCM. Fractions containing product were combined and evaporated in vacuo to give 175 mg (88%) of the title compound as a light yellow solid. MS (ESI–) for $C_{19}H_{17}NO_5S$ m/z 370.1 (M–H)⁻.

Example 7

Preparation of 5-{4-[2-(3-chlorophenyl)-2-oxoethoxy]benzyl}-1,3-thiazolidine-2,4-dione

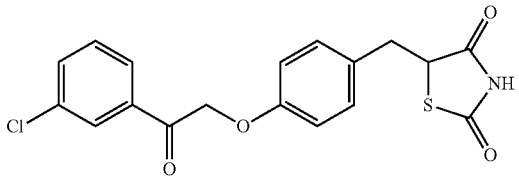

Step 1: 2-(3-chlorophenyl)oxirane.

To a solution of m-chlorostyrene (5.70 g, 41.0 mmol) and acetic acid (2.33 mL, 40.9 mmol) in dioxane (33 ml) and H₂O (78 ml) at 0° C. was added N-bromosuccinimide (8.02 g, 45.0 mmol) in three portions. The reaction was allowed to warm to R.T. After 4 hours, 2N NaOH (60 ml) was added and the reaction was allowed to stir at RT overnight. The reaction mixture was partitioned between water and EtOAc, and the aqueous phase was extracted with EtOAc. The combined organic phases were washed with brine, dried ($Na_2SO_4$), filtered and evaporated in vacuo to give 6.20 g of a slightly tinted oil which was used without further purification.

Step 2: 4-[2-(3-chlorophenyl)-2-hydroxyethoxy]benzaldehyde To a stirring solution of 2-(3-chlorophenyl)oxirane (6.20 g, 40.0 mmol) in toluene (65 ml) was added 4-hydroxybenzaldehyde (7.30 g, 60.0 mmol), 1M NaOH (65 ml) and PEG4000 (polyethylene glycol, 0.85 g) and the stirring mixture was heated at 78° C. for three hours. The reaction was allowed to cool to RT and then extracted with EtOAc (2×150 ml). The combined extracts were washed with brine, dried ($Na_2SO_4$), filtered and evaporated in vacuo. The resulting light brown oil was adsorbed onto silica gel and chromatographed eluting with 25-40% EtOAc/hexanes. There are 2 major spots. Fractions containing the higher Rf spot were combined and evaporated in vacuo to give 1.08 g (10%) of the desired product as a colorless oil. Fractions containing the lower Rf spot were combined and evaporated in vauo to give 0.95 g (8%) of the regioisomer as a colorless oil, 44B. Some starting epoxide (2.85 g) was also recovered.

Step 3: 5-{4-[2-(3-chlorophenyl)-2-hydroxyethoxy]benzylidene}-1,3-thiazolidine-2,4-dione To a stirring solution of 4-[2-(3-chlorophenyl)-2-hydroxyethoxy]benzaldehyde (1.08 g, 3.90 mmol) in absolute EtOH (50 ml) was added 2,4-thiazolidinedione (0.50 g, 4.29 mmol)

and piperidine (0.42 mL, 4.3 mmol), and the resulting solution was heated to reflux and then stirred overnight at room temperature. The reaction mixture was evaporated in vacuo and the residue was dissolved in EtOAc. This solution was washed with aqueous HOAc (pH 5-6), brine, dried ($Na_2SO_4$), filtered and evaporated in vacuo. The residue was adsorbed onto silica gel and chromatographed eluting with 10-20% EtOAc/DCM. Fractions containing product were combined and evaporated in vacuo to give 1.31 g (89%) of the product as a light yellow solid. MS (ESI+) for $C_{18}H_{14}ClNO_4S$ m/z 375.0 $(M+H)^+$. MS (ESI−) for $C_{18}H_{14}ClNO_4S$ m/z 374.1 $(M-H)^-$.

Step 4: 5-{4-[2-(3-chlorophenyl)-2-hydroxyethoxy]benzyl}-1,3-thiazolidine-2,4-dione 5-{4-[2-(3-chlorophenyl)-2-hydroxyethoxy]benzylidene}-1,3-thiazolidine-2,4-dione (0.74 g, 2.00 mmol) was dissolved in THF (20 ml). Water (20 ml) was added and then more THF was added until all solids dissolved. A small crystal of cobalt chloride was added, followed by 2,2'-bipyridine (69 mg, 0.44 mmol). The reaction mixture was cooled to 0° C. $NaBH_4$ was added in portions until the blue color persisted. The color gradually faded and was regenerated repeatedly by small additions of borohydride and HOAc. When HPLC indicated that the reaction was complete, the reaction mixture was partitioned between EtOAc and $H_2O$. HOAc was added until the pH of the aqueous phase was ca. 6, and then the aqueous phase was extracted with EtOAc. The combined organic phases were washed with brine, dried ($Na_2SO_4$), filtered and evaporated in vacuo. The residue was chromatographed on a small silica gel column eluting with 0-10% EtOAc/DCM. Fractions containing product were combined and evaporated in vacuo to give 0.44 g (59%) of a sticky yellow solid. MS (ESI−) for $C_{18}H_{16}ClNO_4S$ m/z 376.1 $(M-H)^-$.

Step 5: Preparation of 5-{4-[2-(3-chlorophenyl)-2-oxoethoxy]benzyl}-1,3-thiazolidine-2,4-dione To a stirring solution of phosphorus pentoxide (0.38 g, 1.30 mmol) in DCM (8 ml) at 0° C. was added a solution of 5-{4-[2-(3-chlorophenyl)-2-hydroxyethoxy]benzyl}-1,3-thiazolidine-2,4-dione (0.25 g, 0.66 mmol) in DCM (8 ml) followed by dimethyl sulfoxide (0.23 mL, 3.30 mml). After stirring for 15 minutes N,N-diisopropylethylamine (0.34 mL, 2.00 mmol) was added. After 45 minutes the reaction was poured into cold sat'd $NaHCO_3$ and the mixture was extracted with EtOAc (x2). The combined extracts were washed with brine, dried ($Na_2SO_4$), filtered and evaporated in vacuo. The residue was chromatographed on a small silica gel column eluting with 0-15% EtOAc/DCM. Fractions containing product were combined and evaporated in vacuo to give 117 mg (47%) of a white solid. MS (ESI−) for $C_{18}H_{14}ClNO_4S$ m/z 374.1 $(M-H)^-$.

Example 8

Preparation of 5-{4-[2-(2-chlorophenyl)-2-oxoethoxy]benzyl}-1,3-thiazolidine-2,4-dione The title compound can be prepared as described in Example 7 using appropriate starting materials, such as 2-(2-chlorophenyl)oxirane.

Example 9

Preparation of 5-{4-[2-(4-methoxyphenyl)-2-oxoethoxy]benzyl}-1,3-thiazolidine-2,4-dione The title compound was prepared as described in Examples 5 and 6 using appropriate starting materials, such as 2-(4-methoxyphenyl)oxirane. MS (ESI−) for $C_{19}H_{17}NO_5S$ 370.2 m/z (M−1).

Example 10

Assays

Assays for Measuring Reduced PPARγ Receptor Activation

Whereas activation of the PPARγ receptor is generally believed to be a selection criteria to select for molecules that may have anti-diabetic and insulin sensitizing pharmacology, this invention finds that activation of this receptor should be a negative selection criterion. Molecules will be chosen from this chemical space because they have reduced, not just selective, activation of PPARγ. The optimal compounds have at least a 10-fold reduced potency as compared to pioglitazone and less than 50% of the full activation produced by rosiglitazone in assays conducted in vitro for transactivation of the PPARγ receptor. The assays are conducted by first evaluation of the direct interactions of the molecules with the ligand binding domain of PPARγ. This can be performed with a commercial interaction kit that measures the direct interaction by florescence using rosiglitazone as a positive control. Further assays can be conducted in a manner similar to that described by Lehmann et al. [Lehmann J M, Moore L B, Smith-Oliver T A: An Antidiabetic Thiazolidinedione is a High Affinity Ligand for Peroxisome Proliferator-activated Receptor (PPAR) J. Biol. Chem. (1995) 270: 12953] but will use luciferase as a reporter as in Vosper et al. [Vosper, H., Khoudoli, G A, Palmer, C N (2003) The peroxisome proliferators activated receptor d is required for the differentiation of THP-1 moncytic cells by phorbol ester. Nuclear Receptor 1:9]. Compound stocks will be dissolved in DMSO and added to the cell cultures at final concentrations of 0.1 to 100 µM and the relative activation will be calculated as induction of the reporter gene (luciferase) as corrected for by the expression of the control plasmid (coding for galactosidase). Pioglitazone and rosiglitazone will be used as reference compounds as described above.

In addition to showing the reduced activation of the PPARγ receptor in vitro, the compounds will not produce significant activation of the receptor in animals. Compounds dosed to full effect for insulin sensitizing actions in vivo (see below) will be not increase activation of PPARγ in the liver as measured by the expression of a P2, a biomarker for ectopic adipogenesis in the liver [Matsusue K, Haluzik M, Lambert G, Yim S-H, Oksana Gavrilova O, Ward J M, Brewer B, Reitman M L, Gonzalez F J. (2003) Liver-specific disruption of PPAR in leptin-deficient mice improves fatty liver but aggravates diabetic phenotypes. J. Clin. Invest.; 111: 737] in contrast to pioglitazone and rosiglitazone, which do increase a P2 expression under these conditions.

The insulin sensitizing and antidiabetic pharmacology are measured in the KKA$^Y$ mice as previously reported [Hofmann, C., Lornez, K., and Colca, J. R. (1991). Glucose transport deficiency corrected by treatment with the oral anti-hyperglycemic agent Pioglitazone. Endocrinology, 129:1915-1925.] Compounds are formulated in 1% sodium carboxy methylcellulose, and 0.01% tween 20 and dosed daily by oral gavage. After 4 days of once daily treatment, treatment blood samples are taken from the retro-orbital sinus and analyzed for glucose, triglycerides, and insulin as described in Hofmann et al. Doses of compounds that produce at least 80% of the maximum lowering of glucose, triglycerides, and insulin will not significantly increase the expression of a P2 in the liver of these mice.

Measuring PPARγ Receptor Activation

The ability of several exemplary compounds of the present invention to bind to PPARγ was measured using a commercial binding assay (Invitrogen Corporation, Carlsbad, Calif.) that measures the test compounds abililty to bind with PPAR-LBD/Fluormone PPAR Green complex. These assays were performed on three occasions with each assay using four separate wells (quadruplicate) at each concentration of tested compound. The data are mean and SEM of the values obtained from the three experiments. Rosiglitazone was used as the positive control in each experiment. Compounds were added at the concentrations shown, which range from 0.1-100 micromolar.

Glucose, Insulin, and Triglyceride in Diabetic KKAy Mice Treated with Exemplary Compounds of the Present Invention.

The insulin sensitizing and antidiabetic pharmacology are measured in the $KKA^Y$ mice as previously reported [Hofmann, C., Lornez, K., and Colca, J. R. (1991). Glucose transport deficiency corrected by treatment with the oral anti-hyperglycemic agent Pioglitazone. Endocrinology, 129:1915-1925.]. Compounds are formulated in 1% sodium carboxy methylcellulose, and 0.01% tween 20 and dosed daily by oral gavage. After 4 days of once daily treatment, blood samples are taken from the retro-orbital sinus and analyzed for glucose, triglycerides, and insulin as described in Hofmann et al. Doses of compounds that produce at least 80% of the maximum lowering of glucose, triglycerides, and insulin will not significantly increase the expression of a P2 in the liver of these mice.

Compounds were formulated by suspension and orally dosed to KKAy mice at 93 mg/kg for 4 days. The compounds were first dissolved in DMSO and then placed into aqueous suspension containing 7-10% DMSO, 1% sodium methylcarboxycellulose, and 0.01% Tween 20. On the fifth day, the mice were fasted and blood samples were obtained approximately 18 hours after the last dose. The parameters were measured by standard assay methods. Data are mean and SEM N=6-12 mice.

TABLE B

| | Assay Results | | | |
|---|---|---|---|---|
| | KKAy Mouse | | | % Rosiglitazone binding to PPARg (100 uM vs. 10 uM) |
| | Glucose (Mean/SD) | Insulin (Mean/SD) | TG (Mean/SD) | Glucose (Mean/SD) |
| Vehicle A | 518 | 24 | 284 | |
| | 59 | 5 | 36 | |
| Ex. 1 | 0.71 | 0.13 | 0.56 | 36.5 |
| | 0.03 | 0.02 | 0.05 | 2.4 |
| Ex. 2 | 0.61 | 0.10 | 0.45 | 63.7 |
| | 0.02 | 0.02 | 0.02 | 12.2 |
| Ex. 3 | 0.64 | 0.20 | 0.62 | 97.9 |
| | 0.02 | 0.07 | 0.04 | 4.0 |
| Ex. 4 | 0.62 | 0.24 | 0.46 | 64.8 |
| | 0.05 | 0.05 | 0.07 | 17.5 |
| Ex. 5 | 0.56 | 0.22 | 0.41 | 13.2 |
| | 0.05 | 0.03 | 0.06 | 0.6 |
| Ex. 6 | 0.75 | 1.20 | 0.80 | 76.2 |
| | 0.04 | 0.27 | 0.11 | 5.6 |
| Ex. 7 | 0.54 | 0.59 | 0.43 | 74.4 |
| | 0.03 | 0.33 | 0.04 | 1.4 |
| Ex. 8 | 1.05 | 0.47 | 0.97 | — |
| | 0.03 | 0.04 | 0.10 | |
| Ex. 9 | 1.00 | 0.76 | 0.90 | 37.2 |
| | 0.03 | 0.21 | 0.06 | 5.0 |

Compounds from examples 1, 2, 3, 4 and 5 exhibited a plasma insulin level of less than about 5 ng/ml and example 6 exhibited a plasma insulin level between about 15 and 20 ng/ml; examples 1, 2, 3, 4, and 5 exhibited a plasma triglyceride level of between about 100 and 200 mg/dl and example 6 exhibited a plasma triglyceride level between about 300 and 400 mg/dl; examples 1, 2, 3, 4, and 5 exhibited a plasma gluclose level of between about 350 and 425 mg/dl and example 6 exhibited a plasma gluclose level between about 450 and 525 mg/dl.

The PPARγ-sparing compounds of this invention will be more effective for the treatment of diseases caused by metabolic inflammation such as diabetes and metabolic syndrome by limiting the side effects attributable to direct and partial activation of nuclear transcription factors.

Because the compounds of the present invention exhibit reduced PPARγ activation, it is anticipated that these compounds are suitable for use in combination with other compounds having antidiabetic activity, such as metformin, DDP-4 inhibitors, or other antidibaetic agents that function by differing mechanisms to augment the actions or secretions of GLP1 or insulin. Specifically because of the reduced PPARγ interaction, these compounds will also be useful for treating dyslipidemia associated with metabolic inflammatory diseases combining particularly well with lipid lowering statins such as atorvastatin or the like. It is also anticipated that the combination of a compound of formula I and other antidiabetic compounds will be more effective in treating diabetes than combinations with PPAR-activating compounds as they will avoid side effects associated with PPARγ activation that may include volume expansion, edema, and bone loss.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating diabetes comprising administering to a patient in need thereof a compound selected from

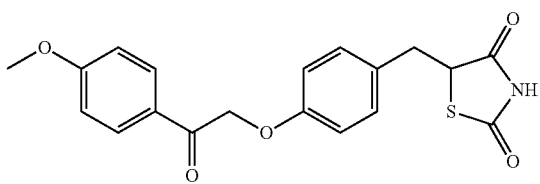

or a pharmaceutically acceptable salt thereof.

2. The method of claim 1, wherein the diabetes being treated is type-2 diabetes.

3. The method of claim 1, wherein the diabetes being treated is type-1 diabetes.

4. A method of treating diabetes comprising administering to a patient in need thereof a pharmaceutical composition comprising a compound selected from

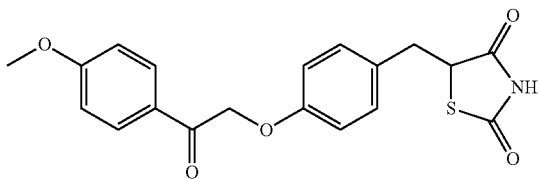

or a pharmaceutically acceptable salt thereof, and a pharmaceutically acceptable carrier.

5. The method of claim 4, wherein the pharmaceutical composition further comprises a DPP-4 inhibitor.

6. The method of claim 5, wherein the DPP-4 inhibitor is selected from sitagliptin, vildagliptin, or any combination thereof.

7. The method of claim 4, wherein the pharmaceutical composition further comprises a GLP-1 agonist, a GLP-2 agonist, or any combination thereof.

8. The method of claim 4, wherein the pharmaceutical composition further comprises a statin.

9. The method of claim 8, wherein the statin is selected from atorvastatin, cerivastatin, fluvastatin, lovastatin, mevastatin, simvastatin, rosuvastatin, pravastatin, or any combination thereof.

* * * * *